(12) United States Patent
Versi

(10) Patent No.: US 11,779,581 B2
(45) Date of Patent: *Oct. 10, 2023

(54) OPIOID FOR USE TO REDUCE AND/OR TREAT DRUG ADDICTION

(71) Applicant: VERSI GROUP, LLC, Gladstone, NJ (US)

(72) Inventor: Ebrahim Versi, Gladstone, NJ (US)

(73) Assignee: DMK PHARMACEUTICALS CORPORATION, Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/575,943

(22) Filed: Jan. 14, 2022

(65) Prior Publication Data

US 2022/0226312 A1    Jul. 21, 2022

Related U.S. Application Data

(62) Division of application No. 16/605,955, filed as application No. PCT/US2018/029685 on Apr. 27, 2018, now Pat. No. 11,246,865.

(60) Provisional application No. 62/492,232, filed on Apr. 30, 2017.

(51) Int. Cl.
  *A61K 31/496* (2006.01)
  *A61P 25/30* (2006.01)
  *A61K 31/135* (2006.01)

(52) U.S. Cl.
  CPC .......... *A61K 31/496* (2013.01); *A61K 31/135* (2013.01); *A61P 25/30* (2018.01)

(58) Field of Classification Search
  CPC ............................. A61K 31/496; A61P 25/30
  See application file for complete search history.

(56) References Cited

U.S. PATENT DOCUMENTS

| | | | |
|---|---|---|---|
| 5,658,908 A | 8/1997 | Chang et al. | |
| 5,807,858 A | 9/1998 | Chang et al. | |
| 5,854,249 A | 12/1998 | Chang et al. | |
| 6,300,332 B1 | 10/2001 | Chang | |
| 6,391,910 B1 | 5/2002 | Zhang et al. | |
| 6,924,288 B2 | 8/2005 | Chang | |
| 7,189,725 B2 | 3/2007 | Chang | |
| 7,795,309 B2 | 9/2010 | Kisak et al. | |
| 8,343,962 B2 | 1/2013 | Kisak et al. | |
| 9,144,553 B2 | 9/2015 | Kisak et al. | |
| 11,246,865 B2 * | 2/2022 | Versi | A61K 31/496 |
| 2002/0052007 A1 | 5/2002 | Chang et al. | |

FOREIGN PATENT DOCUMENTS

| | | |
|---|---|---|
| CN | 103467460 A | 12/2013 |
| WO | WO1993150
62 | 8/1993 |

OTHER PUBLICATIONS

Boswell, E.G. et al. "Synthesis, stereochemistry, and opioid receptor binding activity of heterocyclic analogues of BW373U86", J. Heterocyclic Chem., (1995) 32:1801-1818.

Calderon, S. N. et al. "Probes for Narcotic Receptor Mediated Phenomena. 19.[1] Synthesis of (+)-4-[(αR)-α-((2S,5R)-4-Allyl-2,5-dimethyl-1-piperazinyl)-3-methoxybezyl]-N,N-diethylbonzamide (SNC 80): A Highly Selective, Nonpeptide δ Opioid Receptor Agonist", Journal of Medicinal Chemistry, (1994), 37(14), 2125-8.

Corbett, A. et al. Opioid Receptors, (online), originally retrieved on May 27, 2004, http://opioids.com/receptors/>.

Hamilton, M. "FAQ=Opioid", [online] 1994, [originally retrieved on May 27, 2004], http://opioids.com/opioidfaq/faq.hmtl>.

Knapp, R.J. et al. "Structure-Activity Relationships for SNC80 and Related Compounds at Cloned Delta and Mu Opioid Receptors", Journal of Pharmacology and Experimental Therapeutics, (1996), 277(3), 1284-1291.

Bowen et al. Effects of mixed-action kappa/mu opioids on cocaine self-administration and cocaine discrimination by rhesus monkeys. *Neuropsychopharmacol* 2003:28;1125-1139.

Brito et al. TRPV1: A Potential Drug Target for Treating Various Diseases. *Cells*, 2014:3:517-545.

(Continued)

*Primary Examiner* — Golam M Shameem
(74) *Attorney, Agent, or Firm* — Marianne Fuierer; Casimir Jones, SC

(57) ABSTRACT

The present invention relates to a method of treating drug addiction and reducing dependence or tolerance on a dependence-inducing opiate drug, wherein the method comprises administering to a subject a compound having the structure of formula (I):

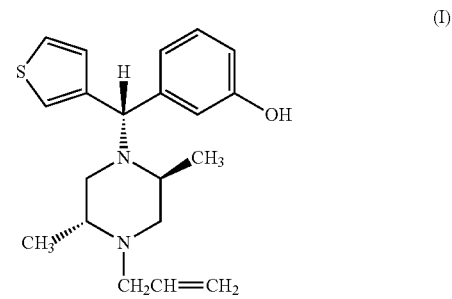

having the IUPAC name of (−)3-((S)-((2S,5R)-4-allyl-2,5-dimethyl-1-piperazinyl)(3-thienyl)methyl)phenol, or pharmaceutically acceptable esters or salts thereof, wherein the compound has activity on the mu, delta and kappa opioid receptors thereby providing added analgesia with an improved therapeutic index and reduced risk of respiratory depression.

9 Claims, 4 Drawing Sheets

(56) References Cited

OTHER PUBLICATIONS

Cheng et al. Relationship between the inhibition constant (K1) and the concentration of inhibitor which causes 50 per cent inhibition (I50) of an enzymatic reaction. *Biochem Pharm*, 1973:22:3099-3108.

Ding et al. Supraspinal actions of nociceptin/orphanin FQ, morphine and substance P in regulating pain and itch in non-human primates. *Br J Pharmacol* 2015:172:3302-3312.

Ding et al. A novel orvinol analog, BU08028, as a safe opioid analgesic without abuse liability in primaes. *Proc Natl Acad Sci U S A*, 2016:113:E5511-5518.

Eisenach et al. Effects of intrathecal ketorolac on human experimental pain. *Anesthesiology*, 2010:112(5):1216-1224.

Funada et al. Blockade of morphine reward through the activation of kappa-opioid receptors in mice. Neuropharmaco, 1993:32: 1315-1323.

Gengo et al. DPI-3290 [(+)-((alpha-R)-alpha-((2S,5R)-4-allyl-2,5-dimetyl-1-piperazinyl)-3-hydroxybenzyl)-N-(3-fluoropheyl)-N-methylbenzamide]. I. A mixed opioid agonist with potent antinociceptive activity. *J Pharmacol Exp Ther*2003, 307:1221-1226.

Gengo et al. DPI-3290 [(+)-((alpha-R)-alpha-((2S,5R)-4-Allyl-2,5-dimetyl-1-piperazinyl)-3-hydroxybenzyl)-N-(3-fluoropheyl)-N-methylbenzamide]. II. A mixed opioid agonist with potent antinociceptive activity and limited effects on respiratory function. *J Pharmacol Exp Ther*2003:307:1227-1233.

Gengo et al. Mixed opioid receptor agonists as a new class of agents for the treatment of moderate to severe pain. I. In *The Delta Receptor*. Edited by Chang K-J, Porreca F, Woods JH: Marcel Dekker; 2004:231-244.

Holder et al. Postoperative pain management. *Int Anesthesiol Clin* 1998:36:71-86.

Hu et al. Long-lasting antinociceptive spinal effects in primates of the novel nociceptin/orphanin FQ receptor agonist UFP-112. *Pain*, 2010:148:107-113.

Ko et al. Relative reinforcing effects of three opioids with different durations of action. *J Pharmacol Exp Ther*, 2002:301:698-704.

Ko et al. Antinociceptive effects of nociceptin-orphain FQ administered intrathecally in monkeys. *J Pain* 2009:10:509-516.

Lavonas et al. Abuse and diversion of buprenorphine sublingual tablets and film. *Journal of substance abuse treatment*2014:47:27-34.

Lazar et al. Screening TRPV1 antagonists for the treatment of pain: lessons learned over a decade. *Expert Opin Drug Discov* 2009:4159-180.

Negus et al. Mu/kappa opioid interactions in rhesus monkeys: implications for analgesia and abuse liability. *Exp Clin Psychopharmacol*, 2008:16:386-399.

O'Neill et al. Antagonistic modulation between the delta opioid agonist BW373U86 and the mu opioid agonist fentayl in mice. *J Pharmacol Exp Ther*, 1997:282:271-277.

Pan. mu-Opposing action of the kappa-opioid receptor. *Trends Pharmacol Sci* 1998:19: 94-98.

Richardson et al. Progressive ratio schedules in drug self-administration studies in rats: a method to evaluate reinforcing efficacy. *Journal of neuroscience methods*, 1996:66:1-11.

Rowlett. A labor-supply analysis of cocaine self-administration under progressive-ratio schedules: antecedents, methodologies, and perspectives. *Psychopharmacology (Berl)* , 200:153:1-16.

Sellers et al. Attractiveness of reformulated OxyContin(R) tablets: assessing comparative preferences and tampering potential. *J Psychopharmacol*, 2013, 27:808-816.

Su et al. Delta-opioid ligands reverse alfentanil-induced respiratory depression but not antinociception. *J Pharmacol Exp Ther*, 1998, 287:815-823.

Van Buskirk et al. Passive transdermal systems whitepaper incorporating current chemistry, manufacturing and controls (CMC) development principles. *AAPS PharmSciTech*, 2012, 13:218-230.

Wang et al. The role of kappa-opioid receptor activation in mediating antinociception and addiction. *Acta Pharmacol Sin*, 2010:31:1065-1070.

Xi et al. Dopamine release in the nucleus accumbens during heroin self-administration is modulated by kappa opioid receptors: an in vivo fast-cyclic voltammetry study. *J Pharmacol Exp Ther*, 1998:284:151-161.

Clotz et al. Clinical uses of fentanyl, sufentanil, and alfentanil. *Clin Pharm* 1991, 10:581-593.

Gutstein et al. Opioid analgesic. In *Goodman and Gilman's The Pharmacological Basis of Therapeutics. 10th Edition*. Edited by Gilman AG, Hardman JG, Limbird LE: McGraw-Hill Companies; 2001:569-619.

Lee et al. Distinct functions of opioid-related peptides and gastrin-releasing peptide in regulating itch and pain in the spinal cord of primates. *Sci Rep*, 2015:5:11676.

\* cited by examiner

OPIOID FOR USE TO REDUCE AND/OR TREAT DRUG ADDICTION

CROSS-REFERENCE TO RELATED APPLICATION

This application is a divisional application of U.S. patent application Ser. No. 16/605,955 filed on Oct. 17, 2019, now U.S. Pat. No. 11,246,865, filed under the provisions of 35 U.S.C. § 371 and claims the priority of International Patent Application No. PCT/US2018/029685 filed on Apr. 27, 2018 which in turn claims priority to U.S. Provisional Patent Application No. 62/492,232, filed on Apr. 30, 2017, the contents of which are hereby incorporated by reference herein for all purposes.

BACKGROUND OF THE INVENTION

Technical Field

The present invention relates to an essentially enantiomerically pure diarylmethylpiperazine compound having utility as an agonist at the principal opioid receptors: mu, delta and kappa, to be used as a therapeutic agent having utility in combating/treating drug addiction and reducing dependence or tolerance on a dependence-inducing opiate drug.

Related Art

Substance addiction is a serious public health problem throughout the world. Heroin and other opioids, including prescription painkillers, are widely abused and account for a large percentage of illicit drug use. Opioid use is also linked to approximately 50% of violent crimes in the United States and costs the U.S. economy billions of dollars per year.

Opioids such as morphine and fentanyl are the mainstay of treatment for chronic moderate-to-severe pain associated mainly with cancer, back injury (~38 million) or osteoarthritis (~17 million).[1] The number of prescriptions for opioids has risen from around 76 million in 1991 to nearly 207 million in 2013.[2] The US is the biggest global consumer, accounting for almost 100% of the world consumption of hydrocodone and 81% of oxycodone.[3]

Sadly, the use of opioids has major complications—the risk of death from breathing cessation and a high probability of dependency. The latter has become an epidemic of abuse and addiction and is regarded by many as a national crisis. It is estimated that between 26.4 and 36 million people abuse opioids worldwide.[4] An estimated 467,000 people in the US are addicted to heroin, 2.1 million suffered from substance use disorders related to prescription opioid pain relievers in 2012[5]—both trends which are on the rise. The number of unintentional overdose deaths from prescription pain relievers has soared in the US, more than quadrupling since 1999. There is also growing evidence to suggest a relationship between increased non-medical use of opioid analgesics and heroin abuse in the United States.[6]

Addiction has two components, tolerance and dependence. Tolerance is the decreased analgesic effectiveness of a drug with continued use. Its consequence is the necessity to increase the administered dose of the drug to maintain the necessary analgesic effect. In the case of the opiates, particularly morphine, the side effects of prolonged use at the very high doses that sometimes need to be given to sustain analgesia can produce life threatening results. Tolerance is an effect thus seen during the course of analgesic administration. By contrast, dependence is an effect seen only after termination of the repeated administration of a drug. Upon termination, a drug dependent subject experiences mild to severely harsh and unpleasant withdrawal symptoms. Despite the desperately recognized need for drugs which reduce tolerance and dependence and produce no unwanted side effects, the search for such drugs has, up to the time of this invention, been unsuccessful.

With concerns that current opioid pain medications can be misused, abused or diverted, physicians are increasingly reluctant to prescribe opiates, resulting in under-treatment of patients suffering from chronic pain, a further driver to seek out illegal non-prescription drugs for relief. Addressing dependency and abuse are high medical and governmental priorities. Better education, tighter restrictions on prescription of opioid drugs, and various abuse deterrent ("AD") technologies are all being pursued. Hitting targets other than the opioid receptors, or receptors involved in downstream signaling are also notable. Unfortunately, Trevena's bias ligand approach has been disappointing as early clinical trial results evidenced typical opiate-related side effects. The trials on systemic use of TRPV1 antagonists have also been disappointing for safety reasons as TRPV1 receptors are ubiquitous.

Acute withdrawal from drug dependence is characterized by dramatic and traumatic symptoms, including sweating, racing heart, palpitations, muscle tension, tightness in the chest, difficulty breathing, tremor, nausea, vomiting, diarrhea, grand mal seizures, heart attacks, strokes, hallucinations and delirium tremens (DTs). Once acute withdrawal symptoms have subsided, post-acute withdrawal syndrome can last for months or years. Post-acute withdrawal symptoms include fatigue, depression, lack of motivation, and increased pain sensitivity.

The reality is that no available non-opioid drug is powerful enough to combat severe pain. However, it would be advantageous to mimic the activities of endogenous opioid peptides, namely to hit not only the mu-subtype of the opioid receptor,[7-9] to which morphine and fentanyl bind and activate selectively, but also the delta and kappa subtypes. The endogenous opioid system comprises several well recognized opioid peptides, referred to as endorphins, which collectively activate the three classical opioid receptor subtypes known as mu, delta and kappa. The pharmacological properties of these opioid receptor classes are clearly differentiated. Commonly prescribed opioids, such as morphine and fentanyl, produce their therapeutic benefit as well as their addictive and adverse effects by selectively binding to and activating the mu-opioid receptors. Clinicians often reduce the dose of these mu-opioid receptor agonists to sub-therapeutic levels to avoid the potentially life-threatening side effect of respiratory depression, and the more common side effects of nausea, vomiting, hypotension, constipation, and urinary retention.[7,10] Delta and kappa agonists on their own provide a limited advantage in treating pain. Delta agonists possess some antinociceptive activity of their own[11] and importantly, also attenuate the respiratory depression caused by mu agonists[12], while enhancing their analgesic effect. Kappa receptor agonists may confer increased analgesia, particularly with visceral pain, and may counteract the abuse potential of mu agonists[13-19].

Numerous treatments have been developed in attempts to ameliorate acute and post-acute withdrawal symptoms. However, in most cases, treatment of withdrawal requires use of other addictive substances (e.g., morphine or methadone). Treatment also requires that the addict attend a clinic daily for an extended amount of time. Due to the severity and duration of withdrawal symptoms, opioid-addicted patients have a high rate of relapse. There is a significant need for effective, non-addictive or less addictive treatment for acute and post-acute opioid withdrawal symptoms.

SUMMARY OF THE INVENTION

The present invention shows that a 'mixed' opioid receptor agonist can provide effective analgesia yet have a broader therapeutic index for safety and dramatically reduce dependency and abuse risks. Patients who still experience pain and are addicted to pain killers such as oxycodone could substitute the addictive drug with DPI-125 to still confer analgesia without reinforcing their addiction. In this way, the patient could be weaned off the addictive drug.

Thus, the present invention relates to a method of reducing and/or treating drug addiction wherein the method comprises administering to a subject a compound DPI-125 having the structure of formula (I):

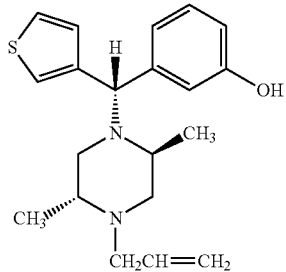

having the IUPAC name of (−)-3-((S)-((2S,5R)-4-allyl-2,5-dimethyl-1-piperazinyl)(3-thienyl)methyl)phenol, or pharmaceutically acceptable esters or salts thereof, wherein the compound has activity on the mu, delta and kappa opioid receptors thereby providing potent analgesia with an improved therapeutic index and reduced risk of respiratory depression with the ability to reduce the euphoric effects associated with mu receptor activation, thereby resulting in reduced abuse potential and hence addiction compared to standard mu opiate agonists.

Tolerance to the analgesic effects of opioids remains a major impediment to the use of these drugs in the treatment of pain. Tolerance is typically a decrease in drug effect with repeated or chronic dosing. Thus, in the treatment of chronic pain, a given dose of the pain killer loses its effect and the patient remains in pain despite the administration of that dose of the opioid. Unfortunately, tolerance to the analgesic effects of opioids can develop rapidly and requires increases in dosage to attain the same analgesic effect. Acute tolerance can also be seen during time-limited opioid administration, such as post-operatively or after trauma. The methods of the present invention are useful in reducing tolerance and/or treating the expression of opioid tolerance or related disorders. The present invention provides for a compound having the beneficial effect for: (1) the effective inhibition of the development of opioid tolerance; (2) reversal or reduction of tolerance to opioids with primary affinity for the mu opioid receptor; (3) reducing opioid dependence; (4) effective inhibition of physical dependence; and (5) reducing or inhibition of addiction.

Thus, the present invention provides for a method for treating and/or reducing opioid tolerance comprising the step of administering to a subject in need thereof a therapeutically effective amount of the compound DPI-125 having the structure of formula (I):

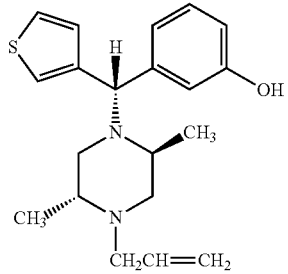

having the IUPAC name of (−)-3-((S)-((2S,5R)-4-allyl-2,5-dimethyl-1-piperazinyl)(3-thienyl)methyl)phenol, or pharmaceutically acceptable esters or salts thereof. The compound DPI-125 can be administered alone or in combination with another opioid.

The co-administered opioid can be selected from such as, for example, morphine, fentanyl, codeine, thebaine, diacetylmorphine (heroin), dihydrocodeine, hydrocodone, hydromorphone, nicomorphine, oxycodone, oxymorphone, alphamethylfentanyl, alfentanil, sufentanil, remifentanil, carfentanyl, ohmefentanyl, nocaine, pethidine (meperidine), ketobemidone, MPPP, allylprodine, prodine, PEPAP, propoxyphene, dextropropoxyphene, dextromoramide, bezitramide, piritramide, methadone, dipipanone, levo-alphacetylmethadol (LAAM), loperamide (used for diarrhea, does not cross the blood-brain barrier), diphenoxylate (used for diarrhea, does not appreciably cross the blood-brain barrier), pentazocine, phenazocine, buprenorphine, etorphine, butorphanol, nalbuphine, levorphanol, levomethorphan, dezocine, lefetamine, tilidine, and tramadol, propoxyphene, or oxycodone. An opioid also encompasses any natural or synthetic narcotic antagonist such as nalmefene, naloxone or naltrexone as well as any natural or synthetic mixed opioid agonist/antagonist such as nalbuphine, butorphanol, buprenorphine or pentazocine; or any pharmaceutically acceptable composition thereof.

In another aspect, the present invention provides for a pharmaceutical composition for inhibition of opioid tolerance and opioid withdrawal-induced hyperalgesia comprising: the compound DPI-125 having the structure of formula (I):

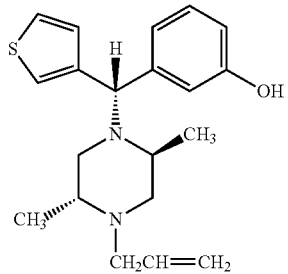

having the IUPAC name of (−)-3-((S)-((2S,5R)-4-allyl-2,5-dimethyl-1-piperazinyl)(3-thienyl)methyl)phenol, or pharmaceutically acceptable esters or salts thereof and a pharmaceutically acceptable carrier.

Examples of pharmaceutically acceptable esters of the compound of formula (I) include carboxylic acid esters of the hydroxyl group in the compound of formula (I) in which the non-carbonyl moiety of the carboxylic acid portion of the ester grouping is selected from straight or branched chain alkyl (e.g., n-propyl, t-butyl, n-butyl), alkoxyalkyl (e.g., methoxymethyl), arylalkyl (e.g., benzyl), aryloxyalky (e.g., phenoxymethyl), and aryl (e.g., phenyl); alkyl-, aryl-, or arylalkylsulfonyl (e.g., methanesulfonyl); amino acid esters (e.g., L-valyl or L-isoleucyl); dicarboxylic acid esters (e.g., hemi succinate); carbonate esters (e.g., ethoxycarbonyl); carbamate esters (e.g., dimethylaminocarbonyl, (2-aminoethyl)aminocarbonyl); and inorganic esters (e.g., mono-, di- or triphosphate).

Pharmaceutically acceptable salts of an amino group include salts of: organic carboxylic acids such as acetic, citric, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as Na+, NH4+, or NX4+ (wherein X is for example a C1-4 alkyl group).

For therapeutic use, salts of the compound of formula (I) is pharmaceutically acceptable, i.e., salts derived from a pharmaceutically acceptable acid. However, salts of acids which are not pharmaceutically acceptable may also find use, for example, in the preparation or purification of a pharmaceutically acceptable compound. All salts, whether or not derived from a pharmaceutically acceptable acid or base, are within the scope of the present invention.

Yet another aspect of the present invention relates to method of treating a patient in need thereof with an opioid receptor agonist therapeutic agent having activity on the mu, delta and kappa receptor, while attenuating respiratory depression incident to the administration thereof, comprising administering to the patient an effective amount of an opioid receptor agonist to attenuate the respiratory depression, the opioid receptor agonist compound DPI-125 having the formula:

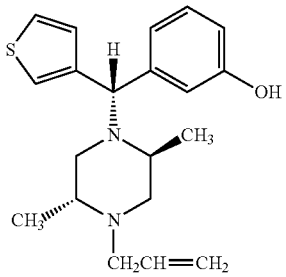

(I)

(−)3-(S)-((2S,5R)-4-allyl-2,5-dimethyl-1-piperazinyl)(3-thienyl)methyl)phenol, or esters or salts thereof.

Yet another aspect of the present invention relates to a pharmaceutical composition comprising:
(a) an effective amount of a bioactive agent for treatment of a condition selected from the group consisting of drug addiction, drug overdose or drug tolerance; and
(b) an effective amount of a compound comprising the formula:

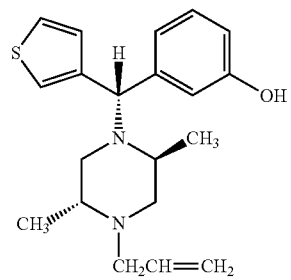

(I)

(−)3-(S)-((2S,5R)-4-allyl-2,5-dimethyl-1-piperazinyl)(3-thienyl)methyl)phenol or a pharmaceutically acceptable salt or esters thereof.

The enantiomerically pure compound of the present invention can be co-administered with a bioactive agent that mediates respiratory depression such as a mu receptor agonist, i.e., various analgesics, and aesthetics, and barbiturates. The vast majority of currently used high potency analgesics, including morphine, alfantanil, morphine-6-glucoronide, oxymorphone, hydromorphone, oxycodone, hydrocodone, fentanyl, meperidine, sufentanyl and codeine, are mu receptor binding compounds. As is well established, these compounds, while highly efficacious for mediating analgesia, have accompanying side effects, including respiratory depression. The use of (−)3-((S)-((2S,5R)-4-allyl-2,5-dimethyl-1-piperazinyl)(3-thienyl)methyl)phenol or ester or salt thereof according to the present invention may prevent, reduce, attenuate or even eliminate or reverse conditions in which analgesia induces respiratory depression, such as the respiratory depression side effects normally attendant to the use of mu receptor binding compounds.

Concerning drug addiction treatment with effective compounds within the broad scope of the present invention, it is noted that methadone is a mu-receptor opiate with actions similar to morphine, i.e., methadone is abusable and addictive. Methadone is used as a "maintenance therapy" agent for opiate addicts, so that such individuals can remain functional while satisfying their addictions in a safer and non-criminal manner. In this respect, DPI-125 has utility in place of, or as an adjunct to, currently used treatments for drug addiction, such as those involving naltrexone, methadone, clonidine, etc.

In a still further aspect, the present invention provides for a method of reducing dependence or tolerance on a dependence-inducing opiate drug, the method comprising administering to a subject in need thereof a therapeutically effective amount of the compound DPI-125 having the structure of formula (I):

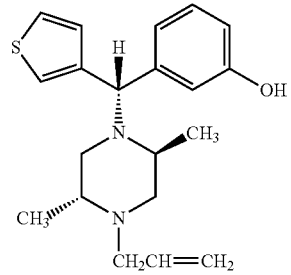

(I)

having the IUPAC name of (−)3-((S)-((2S,5R)-4-allyl-2,5-dimethyl-1-piperazinyl)(3-thienyl)methyl)phenol, or pharmaceutically acceptable esters or salts thereof.

Various other aspects, features and embodiments of the invention will be more fully apparent from the ensuing disclosure and appended claims.

DETAILED DESCRIPTION OF THE INVENTION

Definitions

Figure 1:
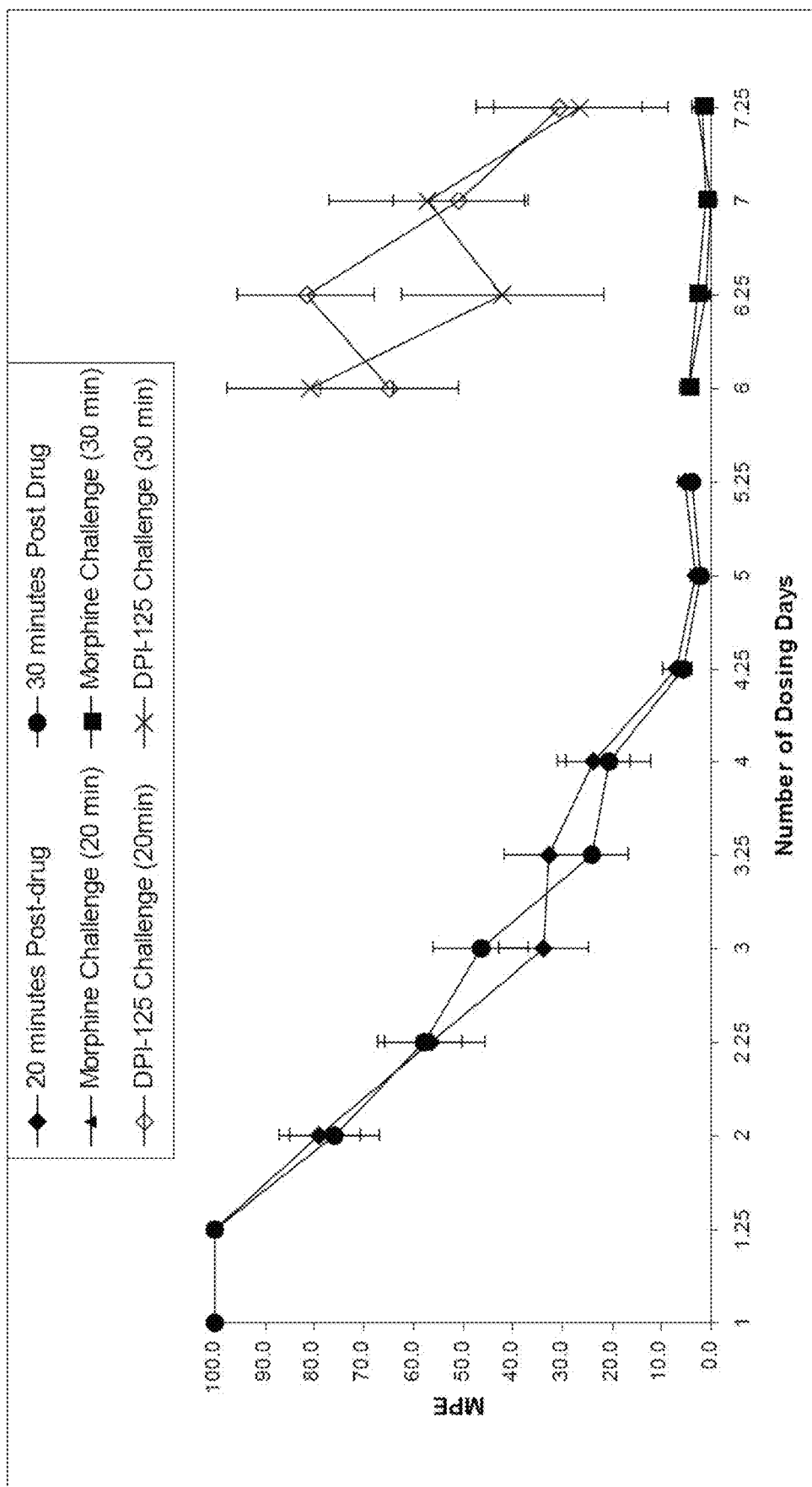
FIG. 1 shows Morphine Tolerance and the Effects of Morphine and DPI-125 Challenge Doses

Unless defined otherwise, all technical and scientific terms used herein have the same meaning as commonly understood by one of ordinary skill in the art to which this invention belongs. As used herein the following terms have the following meanings.

It must be noted that as used herein and in the appended claims, the singular forms "a", "an", and "the" include plural referents unless the context clearly dictates otherwise. Thus, for example, reference to "a compound" includes a plurality of compounds.

The term "about" when used before a numerical designation, e.g., temperature, time, amount, concentration, and such other, including a range, indicates approximations which may vary by (+) or (−) 10%, 5% or 1%.

"Administration" refers to introducing an agent into a patient. Typically, an effective amount is administered, which amount can be determined by the treating physician or the like. Any route of administration, such as oral, topical, subcutaneous, peritoneal, intra-arterial, inhalation, vaginal, rectal, nasal, introduction into the cerebrospinal fluid, or instillation into body compartments can be used. The agent may be administered by direct blood stream delivery, e.g. sublingual, intranasal, or intrapulmonary administration.

The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient.

"Periodic administration" or "periodically administering" refers to multiple treatments that occur on a daily, weekly, or monthly basis. Periodic administration may also refer to administration of DPI-125 or salt or solvate thereof one, two, three, or more times per day. Administration may be via transdermal patch, gum, lozenge, sublingual tablet, intranasal, intrapulmonary, oral administration, or other administration.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

This invention is not limited to any particular chemical form of DPI-125 and the drug may be given to patients either as a free base, solvate, or as a pharmaceutically acceptable acid addition salt.

"Pharmaceutically acceptable composition" refers to a composition that is suitable for administration to a human. Such compositions include various excipients, diluents, carriers, and such other inactive agents well known to the skilled artisan.

"Pharmaceutically acceptable salt" refers to pharmaceutically acceptable salts, including pharmaceutically acceptable partial salts, of a compound, which salts are derived from a variety of organic and inorganic counter ions well known in the art and include, by way of example only, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, oxalic acid and the like, and when the molecule contains an acidic functionality, include, by way of example only, sodium, potassium, calcium, magnesium, ammonium, tetraalkylammonium, and the like.

"Therapeutically effective amount" or "therapeutic amount" refers to an amount of a drug or an agent that, when administered to a patient suffering from a condition, will have the intended therapeutic effect, e.g., alleviation, amelioration, palliation or elimination of one or more manifestations of the condition in the patient. The therapeutically effective amount will vary depending upon the patient and the condition being treated, the weight and age of the subject, the severity of the condition, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of DPI-125, in the context of treating opioid or opioid-like drug dependency, refers to an amount of that attenuates the dependency and/or symptoms of acute withdrawal for at least 1 hours beyond control (placebo), at least 5 hours beyond control, and preferably at least 10 hours beyond control.

A "therapeutic level" of a drug is an amount of DPI-125 or pharmaceutical salt or solvate thereof that is sufficient to treat opioid or opioid-like drug addiction or to treat, prevent, or attenuate acute withdrawal symptoms, but not high enough to pose any significant risk to the patient. Therapeutic levels of drugs can be determined by tests that measure the actual concentration of the compound in the blood of the patient. This concentration is referred to as the "serum concentration."

As defined herein, a "maintenance amount" of a drug is an amount, typically less than the therapeutically effective amount that provides attenuation and/or prevention of post-acute withdrawal syndrome in a patient. The maintenance amount of the compound is expected to be less than the therapeutically effective amount because the level of inhibition does not need to be as high in a patient who is no longer physically addicted to opioid or opioid-like drug. For example, a maintenance amount is preferably 80%, 70%, 60%, 50%, 40%, 30%, 20%, or 10% less than a therapeutically effective amount, or any subvalue or subrange there between.

"Treatment," "treating," and "treat" are defined as acting upon a disease, disorder, or condition with an agent to reduce or ameliorate harmful or any other undesired effects of the disease, disorder, or condition and/or its symptoms. "Treatment," as used herein, covers the treatment of a human patient, and includes: (a) reducing the risk of occurrence of the condition in a patient determined to be predisposed to the condition but not yet diagnosed as having the condition, (b) impeding the development of the condition, and/or (c) relieving the condition, i.e., causing regression of the condition and/or relieving one or more symptoms of the condition. "Treating" or "treatment of" a condition or patient refers to taking steps to obtain beneficial or desired results, including clinical results such as the reduction of symptoms. For purposes of this invention, beneficial or desired clinical results include, but are not limited to: treating opioid or opioid-like drug addiction; opioid tolerance, treating, preventing, and/or attenuating acute withdrawal symptoms; treating, preventing, and/or attenuating long-term (post-acute) withdrawal symptoms; and preventing relapse of opioid or opioid-like drug use.

As used herein, the term "opiate" refers to naturally-occurring alkaloids found in the opium poppy. These include codeine, morphine, oripavine, pseudomorphine, and thebaine. Also included are opium, opium poppy, poppy straw, and extracts and concentrates thereof.

As used herein, the term "opioid" refers to naturally-occurring opiates and synthetic or semi-synthetic opioids that have psychoactive effects. Non-limiting examples include acetyl-alpha-methylphentanyl, acetylmethadol, alfentanil, allylprodine, alphacetylmethadol, alphamethadol, alpha-methylfentanyl, alpha-methylthiofentanyl, alpha-prodine, anileridine, benzylmorphine, benzethidine, beta-cetylmethadol, beta-hydroxyfentanyl, beta-hydroxy-3-methylfentanyl, betameprodine, betacetylmethadol, beta-hydroxyfentanyl, beta-hydroxy-3-methylfentanyl, betameprodine, betamethadol, betaprodine, bezitramide, buprenorphine, butorphanol, carfentanil, clonitazene, codeine, desomorphine, dextromoramide, dextropropoxyphene, dezocine, diampromide, diamorphone, diethylthiambutene, dihydrocodeine, dihydroetorphine, dihydromorphine, dimenoxadol, dimepheptanol, dimethyl-thiambutene, dioxaphetyl butyrate, diphenoxylate, difenoxin, dipipanone, eptazocine, ethoheptazine, ethylmethylthiambutene, ethylmorphine, etonitazene, etorphine, etoxeridine, fentanyl, furethidine, heroin, hydrocodone, hydromorphone, hydroxypethidine, isomethadone, ketobemidone, levoalphacetylmethadol, levomethorphan, levorphanol, levophenacylmorphan, levomoramide, lofentanil, loperamide, laudanum, meperidine, meptazinol, metazocine, methadone, 3-methylfentanyl, 3-methylthiofentanyl, metopon, morphine, morpheridine, MPPP (1-methyl-4-phenyl-4-propionoxypiperidine), myrophine, narceine, nicomorphine, noracymethadol, norlevorphanol, normethadone, nalorphine, nalbuphene, normorphine, norpipanone, opium, oxycodone, oxymorphone, papaveretum, para-fluorofentanyl, paregoric, PEPAP (1-(-2-phenethyl)-4-phenyl-4-acetoxypiperidine), pentazocine, phenadoxone, phenampromide, phenomorphan, phenazocine, phenoperidine, piminodine, piritramide, propheptazine, promedol, properidine, propiram, propoxyphene, racemoramide, racemethorphan, racemorphan, remifentanil, sufentanil, tapentadol, thiofentanyl, tilidine, tramadol, trimeperidine, mixtures of any of the foregoing, salts of any of the foregoing, derivatives of any of the foregoing, and the like. The term opioids also encompasses opioid intermediates, including 4-cyano-2-dimethylamino-4,4-diphenyl butane, 2-methyl-3-morpholino-1,1-diphenyl-propane-carboxylic acid, 4-cyano-1-methyl-4-phenylpiperidine, ethyl-4-phenylpiperidine-4-carboxylate, and 1-methyl-4-phenylpiperidine-4-carboxylic acid. Many opioids are Schedule I or Schedule II drugs in the US.

As used herein, the term "opioid-like drug" refers to any drug that binds to one or more opioid receptor and causes opioid-like addiction. Acute and long-term withdrawal symptoms from cessation of use of such drugs may be similar to those from cessation of opioids. Opioid-like drugs include amphetamine, methamphetamine, ketamine, and cocaine.

As used herein, the terms "addiction" and "dependence" are used interchangeably to refer to the patient's inability to stop using the opioid or opioid-like drug, even when it would be in his/her best interest to stop. The DIAGNOSTIC AND STATISTICAL. MANUAL OF. MENTAL DISORDERS. FOURTH EDITION. TEXT REVISION (DSMIV-TR) criteria for dependency include: Dependence or significant impairment or distress, as manifested by 3 or more of the following during a 12 month period: 1. Tolerance or markedly increased amounts of the substance to achieve intoxication or desired effect or markedly diminished effect with continued use of the same amount of substance; 2. Withdrawal symptoms or the use of certain substances to avoid withdrawal symptoms; 3. Use of a substance in larger amounts or over a longer period than was intended; 4. Persistent desire or unsuccessful efforts to cut down or control substance use; 5. Involvement in chronic behavior to obtain the substance, use the substance, or recover from its effects; 6. Reduction or abandonment of social, occupational or recreational activities because of substance use; 7. Use of substances even though there is a persistent or recurrent physical or psychological problem that is likely to have been caused or exacerbated by the substance.

The term "solvate" as used herein refers to complexes with solvents in which DPI-125 is reacted or from which DPI-125 is precipitated or crystallized. For example, a complex with water is known as a "hydrate". Solvates of DPI-125 are within the scope of the invention. It will be appreciated by those skilled in organic chemistry that many organic compounds can exist in more than one crystalline form. For example, crystalline form may vary based on the solvate used. Thus, all crystalline forms of DPI-125 or the pharmaceutically acceptable solvates thereof are within the scope of the present invention.

DPI-125 of the present invention does not have seizure liability nor does it exhibit dysphoria as a side effect in the first in human trial. Clearly an agonist with the ability to bind not only to the mu subtype, but also to the delta and the kappa subtypes offers a better approach. Mixed mu and delta opioid receptor agonists offer a clinical advantage of providing added analgesia with an improved therapeutic index and reduced risk of respiratory depression. Adding, kappa agonist activity has been shown to reduce the euphoric effects associated with mu receptor activation, potentially resulting in reduced abuse potential compared to standard mu opiate agonists. There is no molecule with the agonist receptor profile of DPI-125 on the market or in development.

The present invention relates to a substantially enantiomerically pure compound of the formula:

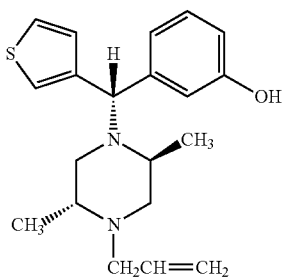

(I)

(−)3-(S)-((2S,5R)-4-allyl-2,5-dimethyl-1-piperazinyl)(3-thienyl)methyl)phenol, or esters or salts thereof.

The compound of formula (I), also referred to as DPI-125, acts as a delta-opioid agonist in the mouse vas deferens delta receptor subtype, as well as an agonist at the delta receptor in the mouse brain, an empirically distinguishable delta receptor subtype from the delta receptor in the mouse vas deferens. Also, the compound has activity at the mu-opioid receptor and exhibits affinity for the kappa receptor.

Subjects to be treated by the methods of the present invention include both human and non-human animal (e.g., bird, dog, cat, cow, horse) subjects, and are preferably mammalian subjects, and most preferably human subjects.

Depending on the specific condition to be treated, animal subjects may be administered the compound of formula (I) at any suitable therapeutically effective and safe dosage, as may readily be determined within the skill of the art, and without undue experimentation.

In general, while the effective dosage of the compound of the invention for therapeutic use may be widely varied in the broad practice of the invention, depending on the specific application, condition, or disease state involved, as readily determinable within the skill of the art, suitable therapeutic doses of the formula (I) compound or esters or salts thereof, for each of the appertaining compositions described herein, and for achievement of therapeutic benefit in treatment of each of the conditions described herein, typically in the range of 0.01 microgram (µg) to 50 milligrams (mg) per kilogram body weight of the recipient, and preferably in the range of 5 µg to 20 mg per kilogram body weight and depending on the route of administration.

The desired dose is preferably presented as once, two, three, four, five, six, or more sub-doses administered at appropriate intervals throughout the day. Alternatively, if the condition of the recipient so requires, the doses may be administered as a continuous infusion or continuous exposure through a depot formulation.

The mode of administration and dosage forms will of course affect the therapeutic amount of the compound that is desirable and efficacious for the given treatment application. For example, orally administered dosages typically are at least twice, e.g., 2-10 times, the dosage levels used in parenteral administration methods, for the same active ingredient.

The compound of formula (I) may be administered per se as well as in the form of pharmaceutically acceptable ethers, esters, salts, and other physiologically functional derivatives thereof.

The formulations include those suitable for parenteral as well as non-parenteral administration, and specific administration modalities include oral, rectal, topical, nasal, ophthalmic, subcutaneous, intramuscular, intravenous, transdermal, spinal, intrathecal, intra-articular, intra-arterial, subarachnoid, sublingual, oral mucosal, bronchial, lymphatic, and intra-uterine administration. Formulations suitable for parenteral and oral administration are preferred.

When the active agent of formula (I) is utilized in a formulation comprising a liquid solution, the formulation advantageously may be administered parenterally. When the active agent is employed in a liquid suspension formulation, the formulation may be advantageously administered orally, rectally, or bronchially.

When the active agent is utilized directly in the form of a powdered solid, the active agent may advantageously be administered orally or sublingually. Alternatively, it may be administered bronchially, via nebulization of the powder in a carrier gas, to form a gaseous dispersion of the powder which is inspired by the patient from a breathing circuit comprising a suitable nebulizer device.

In some applications, it may be advantageous to utilize the active compound of formula (I) in a "vectorized" form, such as by encapsulation of the active agent in a liposome or other encapsulant medium, or by fixation of the active compound, e.g., by covalent bonding, chelation, or associative coordination, on a suitable biomolecule, such as those selected from proteins, lipoproteins, glycoproteins, and polysaccharides.

The formulations comprising the active compound of formula (I) may conveniently be presented in unit dosage forms and may be prepared by any of the methods well known in the art of pharmacy. Such methods generally include the step of bringing the active compound into association with a carrier which constitutes one or more accessory ingredients. Typically, the formulations are prepared by uniformly and intimately bringing the active compound into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration comprise a sterile aqueous preparation of the active compound, which preferably is isotonic with the blood of the recipient (e.g., physiological saline solution). Such formulations may include suspending agents and thickening agents, liposomes or other microparticulate systems which are designed to target the compound to blood components or one or more organs. The formulations may be presented in unit-dose or multi-dose form.

Nasal spray formulations comprise purified aqueous solutions of the active compound of formula (I) with preservative agents and isotonic agents. Such formulations are preferably adjusted to a pH and isotonic state compatible with the nasal mucous membranes. Formulations for rectal administration may be presented as a suppository with a suitable carrier such as cocoa butter, hydrogenated fats, or hydrogenated fatty carboxylic acids. Ophthalmic formulations are prepared by a similar method to the nasal spray, except that the pH and isotonic factors are preferably adjusted to match that of the eye.

The compounds of the invention may also be delivered through the skin or muscosal tissue using conventional transdermal drug delivery systems, i.e., transdermal "patches" wherein a composition of the present invention is typically contained within a laminated structure that serves as a drug delivery device to be affixed to the body surface. In such a structure, the pharmaceutical composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the active agent-containing reservoir and skin contact adhesive are present as separate and distinct layers, with the adhesive underlying the reservoir which, in this case, may be either a polymeric matrix as described above, or it may be a liquid or gel reservoir, or may take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The present invention also contemplates a process for the preparation of (−)3-((S)-((2S,5R)-4-allyl-2,5-dimethyl-1-piperazinyl)(3-thienyl)methyl)phenol or an ester or salt thereof to synthesize an essentially enantiomerically pure opioid receptor agonist that is substantially free of its stereoisomer.

Such compound is desirably prepared in substantially pure enantiomer form, with an enantiopurity of at least 98% EE, and most preferably at least 99% EE. Enantiomeric excess values provide a quantitative measure of the excess of the percentage amount of a major isomer over the percentage amount of a minor isomer which is present therewith, and may be readily determined by suitable methods well-known and established in the art, as for example chiral high pressure liquid chromatography (HPLC), chiral gas chromatography (GC), nuclear magnetic resonance (NMR) using chiral shift reagents, etc.

The use of (−)3-((S)-((2S,5R)-4-allyl-2,5-dimethyl-1-piperazinyl)(3-thienyl)methyl)phenol or ester or salt thereof according to the present invention may prevent, reduce, attenuate or even eliminate or reverse conditions such as the respiratory depression side effects normally attendant to the use of mu receptor binding compounds.

Thus, the present invention contemplates co-administration of (−)3-((S)-((2S,5R)-4-allyl-2,5-dimethyl-1-piperazinyl)(3-thienyl)methyl)phenol with drug agents mediating respiratory depression, in which the compound of the present invention is administered in an amount effective to combat, e.g., significantly attenuate, and preferably substantially eliminate, the respiratory depression incident to the use of the respiratory depression-mediating agent.

Thus, the compounds of the invention have broad utility in surgical and clinical care applications, to combat the unwanted respiratory depression side effect incident to the use of such commonly used drugs as morphine and fentanyl.

EXAMPLE 1

Set out below is the synthesis scheme for production of (−)3-(S)-((2S,5R)-4-allyl-2,5-dimethyl-1-piperazinyl)(3-thienyl)methyl)phenol.

A solution of 3-bromophenol (400 g, 2.31 mol), tert-butylchlorodimethylsilane (391 g, 2.54 mol), and imidazole (346 g, 5.08 mol) in 5000 mL of dichloromethane was stirred overnight at room temperature. The reaction solution was poured into 2000 mL of water and the layers were separated. The organic layer was washed with 1N aqueous sodium hydroxide solution (3×1500 mL) and water (2×1500 mL) before passing through a pad of silica gel (400 g, silica 60, 230-400 mesh). The silica gel was washed with dichloromethane (2×500 mL), the filtrates were combined and the solvent removed under reduced pressure to give 669 g (98.4%) of 3-(bromophenoxy)-tert-butyldimethylsilane as a clear pale yellow liquid. NMR (300 MHz, $CDCl_3$): δ 0.2 (s, 6H); 1.0 (s, 9H); 6.75 (m, 1H); 7.0 (br s, 1H); 7.1 (m, 2H).

3-tert-Butyldimethylsilyloxyphenylmagnesium bromide was formed by the slow addition of a mixture 3-bromophenoxy-tert-butyldimethylsilane (118 g, 400 mmol) and dibromoethane (15 g, 80 mmol) in 400 mL of inhibitor-free anhydrous tetrahydrofuran to a solution of magnesium turnings (15.5 g, 640 mmol) in 800 mL of inhibitor-free anhydrous tetrahydrofuran at reflux. After stirring for one hour at reflux the light brown clear mixture was cooled to room temperature.

Doubly distilled thiophene-3-carboxaldehyde (2.46 g, 22 mmol), benzotriazole (2.62 g, 22 mmol), (2R,5S)-1-allyl-2,5-trans-dimethylpiperazine (3.39 g, 22 mmol, Chirotech Technology, Ltd., Cambridge, England) and p-toluenesulfonic acid monohydrate (209 mg, 1.1 mmol) were dissolved in 125 mL toluene and heated to a gentle reflux. The water-toluene azeotrope was collected in a Dean-Stark trap over the course of 2.5 hours. The remaining solvent was removed under vacuum. The residue was dissolved in 25 mL anhydrous inhibitor-free tetrahydrofuran and to this was added a solution of 3-tert-butyldimethylsilyloxyphenylmagnesium bromide in tetrahydrofuran (125 mL, 0.32 M) under a nitrogen atmosphere at 20-25° C.

The reaction was stirred at 40° C. for 2 hours and then quenched by the addition of 25 mL of saturated $NH_4Cl$ solution. Anhydrous magnesium sulfate (~5 g) and Celite (~10 g) were added. The mixture was stirred and filtered, and the solvent was removed under reduced pressure. The residue was dissolved in ethyl acetate (200 mL) and washed with 1 N NaOH solution (3×100 mL), water (1×100 mL) and brine (1×100 mL). The solution was then concentrated under reduced pressure.

The dark residue was dissolved in 50 mL anhydrous tetrahydrofuran and tetrabutyl-ammonium fluoride dihydrate (8.63 g, 33 mmol) was added. After stirring for 2 hours the reaction was concentrated and the residue was dissolved in 100 mL of ethyl acetate. The mixture was extracted with dilute $NaHCO_3$ solution (3×75 mL) and with water (1×75 mL). The organic layer was diluted with 100 mL of methyl t-butyl ether and extracted with 1% citric acid solution (3×100 mL). The combined aqueous extracts were vacuum filtered through a 0.45 micron membrane filter and the filtrate adjusted to pH 8.5 using 50% NaOH solution before it was extracted with dichloromethane (2×100 mL). The solution was dried azeotropically when concentrated under reduced pressure. The resulting tan glassy solid (3.6 g, 10.5 mmol, 47.8%) was crystallized from 43 mL of 45:55/2-propanol: water and recrystallized from 20 mL of 1:1/2-propanol: water to yield fluffy, white needle crystals (2.1 g, 6.13 mmol, 28% based on chiral piperazine), $[\alpha]_D^{20}=-8.33°$ (abs. ethanol, c=1.0). $^1H$ NMR (500 MHz, $d_6$-DMSO): δ 9.32 (s, 1H), 7.44 (dd, J=3.2, 4.9 Hz, 1H), 7.15 (s, 1H), 7.13 (t, J=8.25 Hz, 1H), 6.98 (d, J=4.9 Hz, 1H), 6.66-6.70 (m, 3H), 5.73-5.81 (m, 1H), 5.15 (d, J=17.1 Hz, 1H), 5.09 (d, J=10.5 Hz, 1H), 5.02 (s, 1H), 3.20 (br d, J=10.2 Hz, 1H), 2.78 (dd, J=7.3, 7.5 Hz, 1H), 2.68 (dd, J=2.6, 11.3 Hz, 1H), 2.59 (dd, J=1, 9.3 Hz, 1H), 2.44 (br s, 2H), 2.02 (t, J=8.6 Hz, 1H), 1.81 (t, J=8.1 Hz, 1H), 1.09 (d, J=6 Hz, 3H), 0.91 (d, J=6 Hz, 3H).

Calculated for $C_{20}H_{26}N_2OS$: C, 70.14; H, 7.65; N, 8.18; S, 9.36%. Found: C, 70.19; H, 7.58; N, 8.12; S, 9.33%.

EXAMPLE 2

Binding of DPI-125 to Three Opioid Receptors

DPI-125 was evaluated for in vitro opioid receptor affinity in rat brain membranes (μ and δ opioid) and guinea pig cerebellum (κ opioid receptor). Membranes for radioligand binding were prepared from either rat whole brain or guinea pig cerebellum, supplied by Pel-Freeze Biological Inc. (Rogers, Ark.). Tissues were homogenized in 50 mM TRIS (Tris[hydrooxymethyl]aminomethane) buffer (pH 7.4) containing 50 μg/ml soybean trypsin inhibitor, 1 mM EDTA (Ethylenediaminetetraacetic acid), and 100 μM PMSF (Phenylmethylsulfonyl fluoride). The homogenized brain tissues were centrifuged at 500×g for 30 minutes (4° C.) to remove large debris. The supernatant was polytronically sonicated for 10 seconds (P.E. setting of 2, 4° C.). Sucrose solution was then added to a final concentration of 0.35 M using a 10 mM TRIS-Sucrose buffer (pH 7.4) and the brain membranes were then centrifuged at 40,000×g for 30 minutes (4° C.). The membrane pellets were then washed twice in 10 mM TRIS buffer (pH 7.4) containing 50 μg/ml soybean trypsin inhibitor, 1 mM EDTA, and 100 μM PMSF.

Radioligand binding assays were performed in 10 mM TRIS buffer (pH 7.4) containing 50 μg/ml soybean trypsin inhibitor, 1 mM EDTA, 5 mM $MgCl_2$, and 100 μM PMSF. Tritium-labeled DAMGO (μ), Deltorphin II (δ), or U69593 (κ) purchased from New England Nuclear were used as ligands in competitive experiments (2-3×10$^{-10}$ M final concentrations) with non-specific binding defined by 0.5×10$^{-6}$ M Naloxone (purchased from SIGMA Chemical Co.). All binding assays were run at room temperature for 90 minutes and then terminated by rapid filtration on GF/C glass fiber filters (Whatman, Hillsboro, OR) with 50 mM TRIS buffer (4° C., pH 7.4) employing a Brandel Semi-automatic Cell Harvester (Model M48, Brandel, Gaithersburg, MD). The filters were washed twice with 50 mM TRIS buffer (4° C., pH 7.4) and the filters were placed in liquid scintillation cocktail and the bound radioactivity counted on a Beckman LS 6500 scintillation counter. The potency of the compounds in inhibiting the binding of radiolabelled DAMGO (μ), Deltorphin II (δ), or U69593 (κ) was determined from full concentration-effect curves. With the computer program Prism (GraphPad Software Inc., San Diego, CA) the $IC_{50}$ values were determined using a one-site nonlinear regression analysis of the radioligand binding data. The $IC_{50}$ values were then converted to $K_i$ values using the Cheng-Prusoff equation.[35] (DPI-125) Enantiomer of the present invention (−)3-(S)-((2S,5R)-4-allyl-2,5-dimethyl-1-piperazinyl)(3-thienyl)methyl)phenol (SSR) was tested and the results for such binding assays is set forth below in Table I:

TABLE I

| Compound | Rat Brain Membrane $K_i$ (nM) | | Guinea Pig Brain Membrane $K_i$ (nM) |
|---|---|---|---|
| | μ | δ | κ |
| Enantiomer DPI-125 (SSR) | 0.40 | 0.88 | 1.77 |

Results: It is evident that DPI-125 compound exhibits distinct and different binding affinity for the different types of receptors tested. The strong and increased affinity of the compound DPI-125 for both mu and delta and kappa receptors is shown by the very low concentration required to inhibit the binding of the labeled compounds.

EXAMPLE 3

In the rat tail-pinch model, DPI-125 was 47 times more potent than morphine in exhibiting antinociceptive activity. As anticipated, DPI-125 has a much larger therapeutic index (antinociception versus respiratory depression) than morphine. Comparing ED50 values in rats for antinociceptive effects and respiratory depression (increased PaCO2), the therapeutic index for DPI-125 was approximately 7× higher than for morphine (Table 2).

TABLE 2

Reduced Potential for Respiratory Depression with Mixed Opioid Agonists. DPI-125 demonstrates comparable analgesic/antinociceptive capacity to morphine and alfentanil with the substantially reduced side effect of respiratory depression, presenting with a much greater therapeutic index

| Drug | Analgesic $ED_{50}$ Tail Pinch (mg/kg) | Respiratory Depression $ED_{50}$ (mg/kg) | Therapeutic Ratio |
|---|---|---|---|
| Morphine | 2.01 | 4.23 | 2.1 |
| Alfentanil | 0.0034 | 0.0127 | 3.7 |
| DPI-3290 | 0.050 | 0.91 | 18.2 |
| DPI-125 | 0.050 | 0.72 | 14.4 |

The preclinical toxicity profile of DPI-125 was as expected for an opioid compound, with two positive exceptions. First, the emesis often associated with other opioid analgesics did not occur, even at the highest doses given.

Second, DPI-125 did not produce any flushing, reddened mucous membranes or urticaria as seen with IV doses of other opioid analgesics.

Given this positive preclinical data, Good Laboratory Practice (GLP) Investigational New Drug (IND) enabling toxicology studies were performed. DPI-125 was tested in human subjects in a PK and safety study. DPI-125IV.001, was a randomized, single-center, double-blind, placebo-controlled, dose escalating Phase 1 study. The primary objective was to evaluate the safety of single doses of DPI-125 administered by intravenous bolus infusion in normal healthy adult subjects. Male and female subjects between 18 and 55 years of age, inclusive, who were in good health and who were not taking any medications were eligible for enrollment. For each dose group, cohorts of 6 subjects were randomized to receive either placebo (n=1) or DPI-125 for Injection (n=5) as a single bolus dose of 5, 10, 20, or 50 µg/kg administered over 2 minutes. A final cohort received 25 µg/kg administered over 1 minute. For this first in human study, it was decided that 50 µg/kg should be the highest dose to be tested so the maximum tolerated dose was not determined.

DPI-125 for injection was well tolerated; there were no deaths or any other serious AEs reported. Drug-related AEs were generally dose-dependent and all resolved spontaneously; none led to discontinuation. The most common drug-related AEs were somnolence, dizziness, and paraesthesia, interestingly, not nausea or vomiting. No subject had a clinically significant change in vital sign measurements, on physical examination, 12-lead electrocardiogram ("ECG"), or continuous lead-II ECG. No time- or dose-related trends in corrected QT intervals were noted. Overall, electroencephalogram ("EEG") tracings were unremarkable, with no changes associated with the administration of study drug and, in particular, no seizure activity was noted. No subject had a clinically significant change in laboratory results. In conclusion, there were no findings of clinical concern at any dose of DPI-125 tested in this study.

The preliminary studies indicate that DPI-125 has analgesic benefits potentially superior to morphine and comparable to fentanyl but in addition it will have a far better tolerability profile. Notably, it offers a larger safety margin for respiratory depression and may reduce abuse potential. There is currently no drug like DPI-125 (mu, kappa and delta mixed agonists) either on the market or in development. The results indicate that DPI-125 provides analgesic benefits of superior or comparable potency to current opioids (>40x that of morphine) and demonstrates lack of abuse liability by not demonstrating reinforcing effects at doses that achieve strong analgesia in contrast to that observed with currently marketed opioids.

EXAMPLE 4

Evaluation of the analgesic effect of DPI-125 in Non Human Primates (NHPs) at 3 different doses. Capsaicin evokes pain sensation by activating the transient receptor potential vanilloid type 1 which plays a pivotal role in diverse pain states.[23] Capsaicin has been widely utilized as a clinically relevant pain model in humans to study pain processing pathways and to identify potential analgesics.[24,25] A model of capsaicin-induced thermal allodynia has been established and used to evaluate the functional efficacy of clinically used opioids and experimental compounds for alleviating capsaicin-induced hypersensitivity in NHP.[26,27] The study provides for documentation of the functional efficacy of DPI-125 as an analgesic in primates compared to fentanyl.

Briefly, 0.3 mL of capsaicin at 1.2 mg/mL is administered topically via a bandage attached on the terminal 3-5 cm of the tail for 15 min. Capsaicin-induced hypersensitivity peaks at 15 min after removal of the capsaicin bandage and this is the time point used to measure non-human primates' (NHP) behavioral responses (i.e., reversal of reduced tail-withdrawal latency in 46° C. water).[26]

Effects of systemic DPI-125 (0, 0.1, 0.3, and 1 mg/kg, IV) is investigated in the same group of 4 subjects. The dose range of DPI-125 is selected and projected from the active dose range in rodents. Normally, 3 doses are selected to demonstrate a dose dependency for any study endpoint. The dose of DPI-125 will either be increased or decreased based on results of this tentative dose range in order to complete a dose-response study.

For comparison, effects of fentanyl (0.01 mg/kg, IV)[28] is also be tested and used as a positive control in the same subjects. Using a single dosing procedure (i.e., drug pretreatment 20 min before capsaicin), the effectiveness and potency of DPI-125 is determined for alleviating capsaicin-induced hypersensitivity. Based on prior experience across different ligands and experimental settings[29-31], a 1-week inter-injection interval (i.e., NHP subjects are tested once per week) is sufficient to avoid potential confounding factors under these experimental conditions. The order of administration of vehicle and different doses of DPI-125 is randomized and scheduled according to a Latin Square design.

EXAMPLE 5

Evaluation of Reinforcing Behaviour of DPI-125 on IV Drug Self-administration in NHPs: A progressive-ratio (PR) schedule of reinforcement which has been commonly used for evaluating abuse liability[26,32,33] is used to determine the relative reinforcing strength of DPI-125 as compared to another mu opioid analgesic, fentanyl, which exerts high reinforcing strength. The PR schedule measures how many responses subjects will emit in order to receive a drug injection before they cease responding. The advantage of this PR schedule for assessing abuse liability is that it can provide a differentiation among drugs that may function as positive reinforcers.[33] Dose-response curves are determined by substituting vehicle, iv fentanyl (0.0003 mg/kg/injection), and a range of doses of DPI-125 (0.001-0.01 mg/kg/injection) in a random order. These dosing conditions are available for at least five consecutive sessions and until NHP's responses become stable.[26] This study determines whether DPI-125 produces reinforcing strength in comparison to fentanyl as an indication of its abuse potential.

Data Analysis/Statistical Analysis: In the Vertebrate Animals Section, we have justified n=4 NHPs is sufficient to provide the statistical power and it can be used to determine and compare the behavioral effects of DPI-125 by citing several references. For highly addictive drugs like cocaine, the averaged injection numbers by NHPs under the PR schedule are around 12-15. In contrast, the averaged injection number for saline/vehicle is around 3-4.[26] If the averaged injection number earned for DPI-125 (over several doses) is significantly lower than 12 and not significantly different from saline/vehicle, i.e., 3-4, then it is concluded that DPI-125 does not have reinforcing strength, i.e., no concern for its abuse liability.

EXAMPLE 6

As stated above, tolerance is typically a decrease in drug effect with repeated or chronic dosing. In the treatment of chronic pain, the pain killer loses its effect and the subject remains in pain despite the administration of the same dose of opioid.

Three studies were conducted to assess the degree of antinociceptive tolerance produced by chronic administration of DPI-125 and the degree of cross-tolerance to morphine. The objective of study 1 was to demonstrate the presence or absence of cross-tolerance between morphine and DPI-125. The objective of studies 2 and 3 was to evaluate the degree of cross-tolerance in terms of changes in the analgesic ED50 for DPI-125 and morphine. This study was performed in three parts to investigate the development of tolerance to the antinociceptive effects of equi-analgesic doses of DPI-125 and morphine sulfate (morphine) and to identify any cross-tolerance between these two opioid receptor agonists.

After twice daily dosing of 5.0 mg/kg morphine (s.c.) for 5 days or 1.0 mg/kg DPI-125 (s.c.) for 6 days in male Sprague-Dawley rats, tolerance to the antinociceptive effects of both drugs were detected in the rat tail pinch assay. Tolerance did not develop after a single dose of morphine or DPI-125. There was a clear difference in the rate of development of tolerance to morphine and DPI-125 administered in this manner. Maximal tolerance to the antinociceptive effects of morphine was evident at day 5 for dosing, whereas complete tolerance to DPI-125 was not evident until day 8. Animals tolerant to 1.0 mg/kg DPI-125 BID showed complete tolerance to the antinociceptive effects of 5.0 mg/kg morphine. However, animals tolerant to 5.0 mg/kg morphine BID were only partially tolerant to 1.0 mg/kg DPI-125. The antinociceptive ED50 for morphine and DPI-125 was determined in animals exposed to vehicle or exposed and tolerant to either morphine or DPI-125. The results are presented in the table below.

| Drug Treatment | $ED_{50}$ | Confidence Interval | Fold Change |
| --- | --- | --- | --- |
| Morphine to naive animals | 2.037 | 1.509-2.750 | |
| Morphine to morphine tolerant animals | 11.26 | 8.115-15.64 | 5.5 |
| Morphine to DPI-125 tolerant animals | 15.82 | 13.25-18.90 | 7.8 |
| DPI-125 to naïve animals | 0.407 | 0.265-0.625 | |
| DPI-125 to DPI-125 tolerant animals | 1.218 | 1.211-1.226 | 3.0 |
| DPI-125 to morphine tolerant animals | 0.717 | 0.671-0.766 | 1.8 |

In summary, mild DPI-125 tolerance developed over several days of twice daily dosing at 2.0 mg/kg/day. Tolerance to DPI-125 crossed over completely and tolerance to morphine was also present. However, following the development of complete tolerance to morphine (10.0 mg/kg/day), DPI-125 still remained effective as an antinociceptive agent at 2.0 mg/kg/day. Thus tolerance to DPI-125 is not as great as that to morphine.

MATERIALS AND METHODS

Dose solutions were prepared daily just before the first daily dose was administered. Dose solutions of DPI-125 were prepared in 5% Dextrose in water (USP) with an acetic acid/sodium acetate buffer according to the procedure in the study protocol. Dose solutions of morphine sulfate (Sigma-Aldrich) were prepared in 5% Dextrose in water (USP). Dose solutions were stored between doses at room temperature, protected from light.

This study was performed in three parts to investigate the development of tolerance to the antinociceptive effects of equi-analgesic doses of DPI-125 and morphine sulfate (morphine) and to identify any cross-tolerance between these two opioid receptor agonists. The equi-analgesic doses used to induce tolerance to the antinociceptive effects of morphine and DPI-125 were selected based on the antinociceptive ED50 for each compound. ED50 values were taken from both internal and published data and the doses used here were ~2.5 fold the antinociceptive ED50 dose.

Study 1: Male Sprague-Dawley rats were used in this study in two groups of 12 animals. The first group received subcutaneous (s.c) doses of 5.0 mg/kg of morphine sulfate twice a day (doses were 6 hours apart) totaling a daily dose of 10 mg/kg. The second group in this study received subcutaneous doses of 1.0 mg/kg DPI-125 twice daily (doses were separated by 6 hours). Dosing was repeated for 5 days in the case of morphine sulfate administration and for 6 days in the case of DPI-125. The first day of dosing was designated day 1. On day 6 (morphine sulfate treated group) or day 7 (DPI-125 treated group), half the subjects of both groups (i.e. 6 animals) were challenged with a single administration of the drug not received during the first 5 or 6 test days. The other half received the same drug as in the previous 5 or 6 days. On each day, animals were tested for antinociception 20 and 30 minutes following drug administration using the standard tail pinch test. Where complete cross-tolerance was not observed, challenge dosing continued on a twice daily schedule (separated by 6 hours) until complete tolerance to antinociceptive effects were observed, at which time both groups were then euthanized.

Study 2: Dosing and antinociception testing was the same as described in Study 1 using similar sized groups (n=6). All doses were administered subcutaneously twice daily at half the total daily dose. Doses were separated by 6 hours. Antinociceptive drug effects were assessed 20 and 30 minutes after every dose administered using a tail pinch test. As a result of the findings from the first study showing no difference in these time points, only the 20 minute test time was used for in depth analysis. The first day of dosing was designated as day 1. Dose groups and challenge doses are listed in Table 1. Groups 1-3 received a subcutaneous dose of dextrose on days 1-6. On day 7 each group received either a 2.0, 3.0 or 10.0 mg/kg/day dose of morphine sulfate (respectively). Groups 4-7 received 5.0 mg/kg/day morphine sulfate on days 1-6 but received different challenge doses of morphine sulfate on day 7. Challenge doses were 15.0, 20.0 and 25.0 mg/kg/day for groups 4, 5 and 6 respectively. Groups 8-11 received 5.0 mg/kg/day doses of morphine sulfate on day 1-6. On day 7, challenge doses of DPI-125 were administered at doses of 0.5, 1.0, 2.0 and 3.0 mg/kg/day for groups 8, 9, 10, and 11 respectively. A total of 18 animals received control solution for the first six days; a total of 48 animals received morphine sulfate for the first six days.

Study 3: Dosing and antinociception testing was the same as described in Study 1 using similar sized groups (n=6). All doses were administered subcutaneously twice daily at half the total daily dose. Doses were separated by 6 hours. Antinociceptive drug effects were assessed 20 and 30 minutes after every dose administered using a tail pinch test. As a result of the findings from the first study showing no difference in these time points, only the 20 minute test time was used for in depth analysis. The first day of dosing was designated as day 1. Dose groups and challenge doses are listed in Table 2. Groups 12-14 received dextrose on days 1-6. On day 7 these groups received 0.25, 0.5 or 1.0 mg/kg/day of DPI-125, respectively. Groups 15-18 received 1.0 mg/kg/day DPI-125 on days 1-6 and received a challenge dose of 2.25, 2.5, 3.0, 3.5 mg/kg/day of DPI-125 respectively on day 7. Groups 19-22 received 1.0 mg/kg/day doses of DPI-125 on days 1-6. On day 7, these groups received challenge doses of 20.0, 30.0, 40.0, and 50.0 mg/kg/day of morphine sulfate respectively. All groups were euthanized and discarded on Day 7. A total of 18 animals received control solution for the first 6 days; a total of 48 animals received DPI-125 for the first six days.

Antinociception: A trained observer blinded to the drug treatment allocation assessed antinociception using an arterial clamp on the tail, at a point approximately one inch from the tip, at 20 and 30 minutes post-injection. The escape latency was determined by measuring the time from the placement of the clamp to the detection of an escape response (either an attempt to bite the clamp or vocalization). A 20 second cutoff period was used to prevent tissue damage during antinociceptive testing. Drug-induced antinociception was converted to Maximal Percent Effect (MPE) values by expressing the response latency in seconds as a percentage of the maximal response time (20 seconds). No formal statistical analysis of the difference between the antinociception induced by the first and second doses of drug on the first test day was performed to investigate the incidence of tolerance after a single drug dose since, with both morphine sulfate and DPI-125, MPE was 100% for all animals at both dose points and time points on Day 1. Subsequently, for graphical representation, all dose time points were expressed in days numbered from the first dose on the first day of dosing (Day 1) and the second daily dose (6 hours after the first dose) as the quarter day (Day 1.25).

Study 1: Tolerance to the antinociceptive effects of morphine sulfate and DPI-125 was analyzed using analysis of variance over the first 6 days of drug administration and at each tail pinch test time (20 or 30 minutes post-drug). Post-hoc analysis was performed using a Fisher's Predicted Least Squared Difference (FPLSD) test (Statview, SPSS, NC). Challenge doses were compared to the first and last doses of the tolerance schedule (i.e. day 1 and day 5 dose 2 for morphine tolerant animals and day 1 and day 6 dose 2 for the DPI-125 tolerant animals) in a similar manner (ANOVA+FPLSD). The difference between the 20 minute and 30 minute post-dose tail pinch time points was compared using a repeated measures analysis of variance for the morphine and DPI-125 tolerance schedules only (not the challenge dosing). Significant main effects were analyzed using pair wise Student's t-test comparisons. All tests required significance at P<0.05 in a two-tailed test.

Studies 2 and 3: Data from studies 2 and 3 were expressed in MPE as described above. Non-linear regression was used to determine ED50 values for morphine sulfate and DPI-125 in naïve animals and animals tolerant to either morphine sulfate or DPI-125 (Prism, GraphPad Software, CA). ED50 values are presented with 95% confidence intervals as follows: ED50 (lower-upper limit of 95% interval).

RESULTS

Study 1 Tolerance to Morphine Sulfate: FIG. 1 shows the MPE antinociceptive response to 10.0 mg/kg/day (5.0 mg/kg/dose) morphine sulfate over repeated doses/days at both the 20 and 30 minute post-drug time points. Repeated measures analysis of variance showed no significant difference between the tolerance profile of repeated morphine sulfate dosing when antinociception was determined at 20 or 30 minutes post-drug (F(1,132)=0.074; P=0.787).

Tolerance to the antinociceptive effects of morphine sulfate: There was no significant difference between the effect of the first and second morphine sulfate dose on day 1 (100% MPE for all animals at both doses). Significant tolerance to morphine sulfate-induced antinociception developed by the 3rd dose (the first dose on day 2) at both the 20 minute (78.9±7.9%; P<0.05) and 30 minute (78.9±8.6%; P<0.005) post-drug assessment times. Complete desensitization to antinociceptive effects (0% MPE) did not develop on any day at either the 20 or 30 minute assessment times. However, by the second dose of day 4, sufficient tolerance had developed that morphine sulfate produced a mean MPE of 7.0±2.8% at 20 minutes post-drug (P<0.0001 v. dose 1) and 5.7±1.8% at 30 minutes post-drug (P<0.0001 v. dose 1). The lowest MPE value was produced after the first dose day 5 and produced a mean MPE of only 3.1±1.2% (P<0.0001 v. dose 1) 20 minute post-drug and 2.2±1.0% (P<0.0001 v. dose 1) at 30 minutes post-drug. Maximal tolerance to morphine developed at 5 days of b.i.d dosing.

Figure 2:
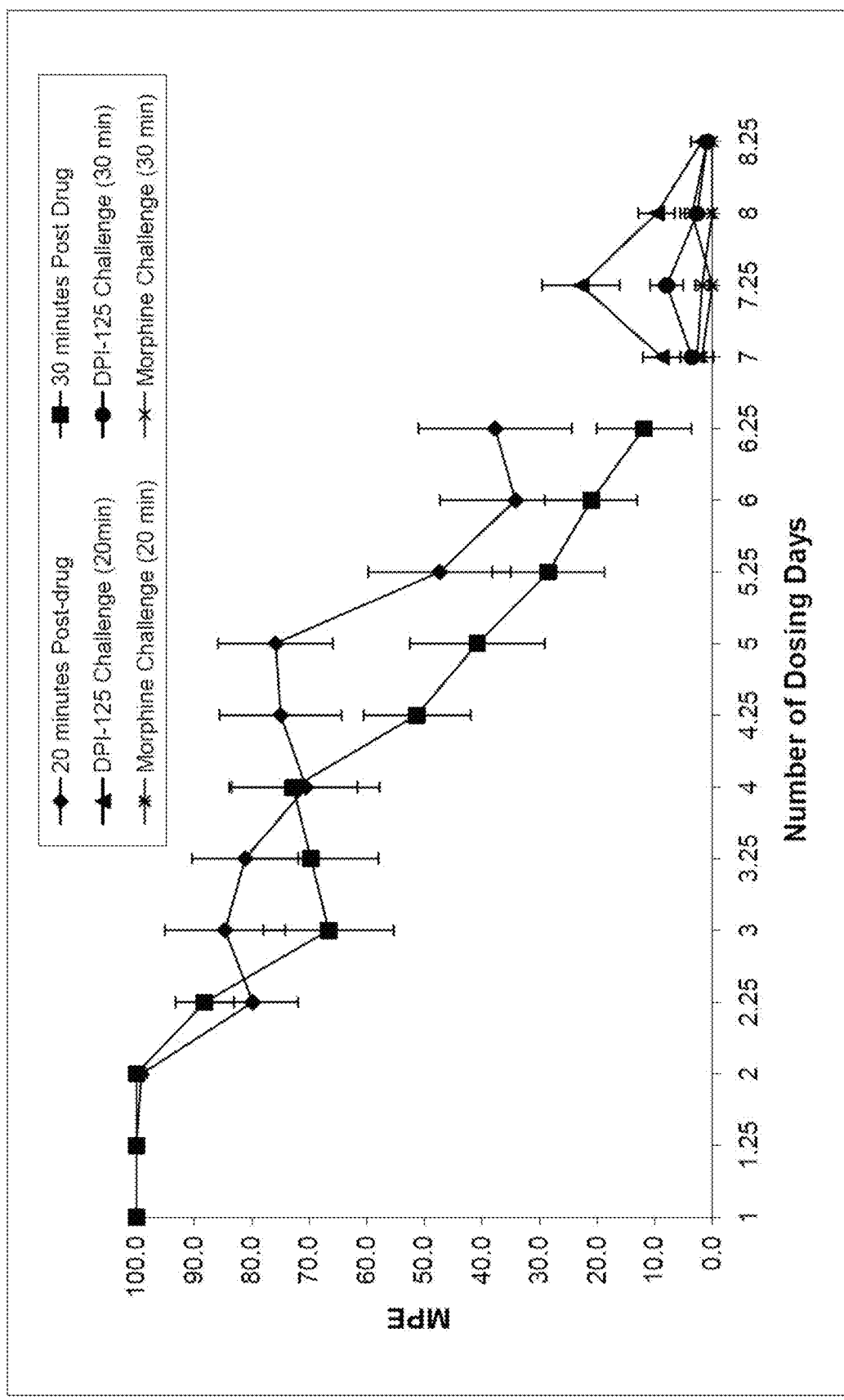
FIG. 2 shows DPI-125 Tolerance and the Effects of Morphine and DPI-125 Challenge Doses.

Tolerance to DPI-125: FIG. 2 shows the MPE antinociceptive response to 2.0 mg/kg/day (1.0 mg/kg/dose) DPI-125 over repeated doses/days at both the 20 and 30 minute post-drug time points. Repeated measures analysis of variance indicated that there was a significant difference between the tolerance profile of the antinociceptive action of repeated DPI-125 dosing (P<0.0001). Further analysis with pair wise Student's t-tests demonstrated a significant difference between the antinociceptive effects of DPI-125 recorded 20 minutes and 30 minutes after the 5th dose (the first dose of day 3; MPE 84.7±10.0% at 20 minutes and 66.7±10.9% at 30 minutes post-drug; P<0.05), the 9th dose (the first dose of day 5; MPE 75.9±9.5% at 20 minutes and 40.8±11.2% at 30 minutes post-drug; P<0.05) and the 10th dose (the second dose of day 5; MPE 47.4±11.9% at 20 minutes and 28.5±9.3% at 30 minutes) of DPI-125.

Tolerance to antinociceptive action measured 20 minutes post-drug: When the antinociceptive activity of DPI-125 was measured 20 minutes post-drug, significant tolerance developed by the first dose of day 4 (MPE 70.6±12.3%; P<0.05 v. dose 1) and was present at the 10th, 11th and 12th doses (dose 2 of day 5 and doses 1 and 2 of day 6: MPE 47.4±11.9%, 34.2±12.5%, 37.7±12.7% respectively; P<0.0001 v. dose 1). Maximum tolerance (0% MPE) was not present by the end of 6 days of dosing (after the 12th dose), although the two doses on day 6 produced MPE of 34.2±12.5% and 37.7±12.7% respectively. During the DPI-125 challenge dosing period (days 7 and 8), however, the MPE did reach as low as 1.8±1.8% (the second dose of day 8). Complete tolerance to DPI-125 developed at 8 days of b.i.d. dosing.

Tolerance to antinociceptive action measured 30 minutes post-drug: When the antinociceptive activity of DPI-125 was measured 30 minutes after dosing, significant tolerance was developed by the first dose of day 3 (MPE 66.7±10.9%; P<0.005 v. dose 1) and was present through all subsequent doses (FIG. 2, Table 4). As with the 20 minute time point, complete tolerance was not developed after any of the 12 doses administered, although the last dose (second dose of day 6) produced an MPE of 11.8±7.9% which was significantly lower than the lowest MPE recorded at 20 minutes (34.2±12.5%; P<0.05).

Morphine Challenge to Morphine tolerant animals: As described above, morphine tolerance was established through twice daily subcutaneous dosing of 5.0 mg/kg morphine sulfate for 5 days. Morphine sulfate was administered in a similar manner on days 6, 7, and 8. The antinociceptive effects of the morphine sulfate challenge doses are presented in FIG. 1. Challenge doses of morphine sulfate produced significantly less antinociception than the first dose on day 1 (P<0.0001 for all comparisons) but there was no significant difference between the antinociception produced by any challenge dose and the last dose of the 5 days of tolerance development (P>0.05 for all comparisons: Table 3). This persistent tolerance to morphine sulfate was evident at both the 20 and 30 minute test time-points.

Morphine Challenge to DPI-125 tolerant animals: Following the establishment of tolerance to the antinociceptive effects of DPI-125 (1.0 mg/kg) over 6 days of dosing, twice daily challenge doses of morphine (5.0 mg/kg) produced significantly less antinociception than the first day of DPI-125 dosing (at both the 20 and 30 minutes time points (P<0.0001 for all comparisons between days 7 and 8 and day 1 dose 1). Further to this, there was no significant difference between the antinociception produced by the final dose of DPI-125 used to establish antinociceptive tolerance and any of the morphine challenge doses either 20 or 30 minutes post-drug (P>0.05 for all comparisons; Table 3). There was no significant difference between the antinociception produced by morphine sulfate (5.0 mg/kg) doses after tolerance had been established to either morphine sulfate (5.0 mg/kg) or DPI-125 (1.0 mg/kg) (P>0.05 for Student's t-test comparisons between parallel test days).

DPI-125 Challenge to DPI-125 tolerant animals: DPI-125 tolerance was induced through twice daily doses of 1.0 mg/kg for 6 days at which point the antinociceptive MPE was 37.7±12.7% 20 minutes post-drug and 11.8±7.9% 30 minutes post-drug. Despite the lack of induction of complete tolerance (0% MPE) to DPI-125, challenge doses of 1.0 mg/kg twice daily for 2 days produced significantly less antinociception than the first dose of the tolerance schedule (P<0.0001 for all comparison at both 20 and 30 minute antinociceptive assessments). At the 20 minute antinociceptive assessment there were significantly attenuated antinociceptive responses to all challenge doses tested when compared with the effect of the last tolerance dose (P<0.05 for all comparisons; Table 4). However, at the 30 minute post-drug test time point there was no significant difference between the antinociceptive effects of any challenge dose relative to the last dose of the tolerance schedule (P>0.05; FIG. 2).

DPI-125 Challenge to Morphine tolerant animals: Following the establishment of tolerance to the antinociceptive effects of morphine sulfate (as described above), twice daily challenge doses of DPI-125 (1.0 mg/kg) produced significantly less antinociception than the first tolerance dose at all challenge doses (P<0.0001; Table 4) except the second dose on the first challenge day (day 6) when antinociception was recorded 20 minutes post-drug (P>0.05). However, when antinociception was recorded 30 minutes post-drug, all challenge doses produced significantly less antinociception than the first tolerance dose (P<0.0001; Table 4) except for the first challenge dose (day 6 dose 1; P>0.05). More critically, however, DPI-125 challenge to morphine tolerant animals produced clearly and significantly higher levels of antinociception than the last tolerance doses of morphine, or than the morphine challenge doses (P<0.0005; FIG. 2). This antinociceptive efficacy of DPI-125 challenge doses was evident for the first 4 challenge doses at the 20 minute post-drug test time point but just the first 3 challenge doses when antinociceptive testing was carried out 30 minutes post-drug. The maximum level of antinociception produced by any single DPI-125 challenge dose (MPE 81.6±12.6% at 20 minutes and 80.7±15.2% at 30 minutes) was approximately equivalent to the effect of the same DPI-125 dosing after 6 repeated doses in naïve animals when measured at the 20 minute time point and after 5 repeated doses when measured at the 30 minute time point.

Figure 3:
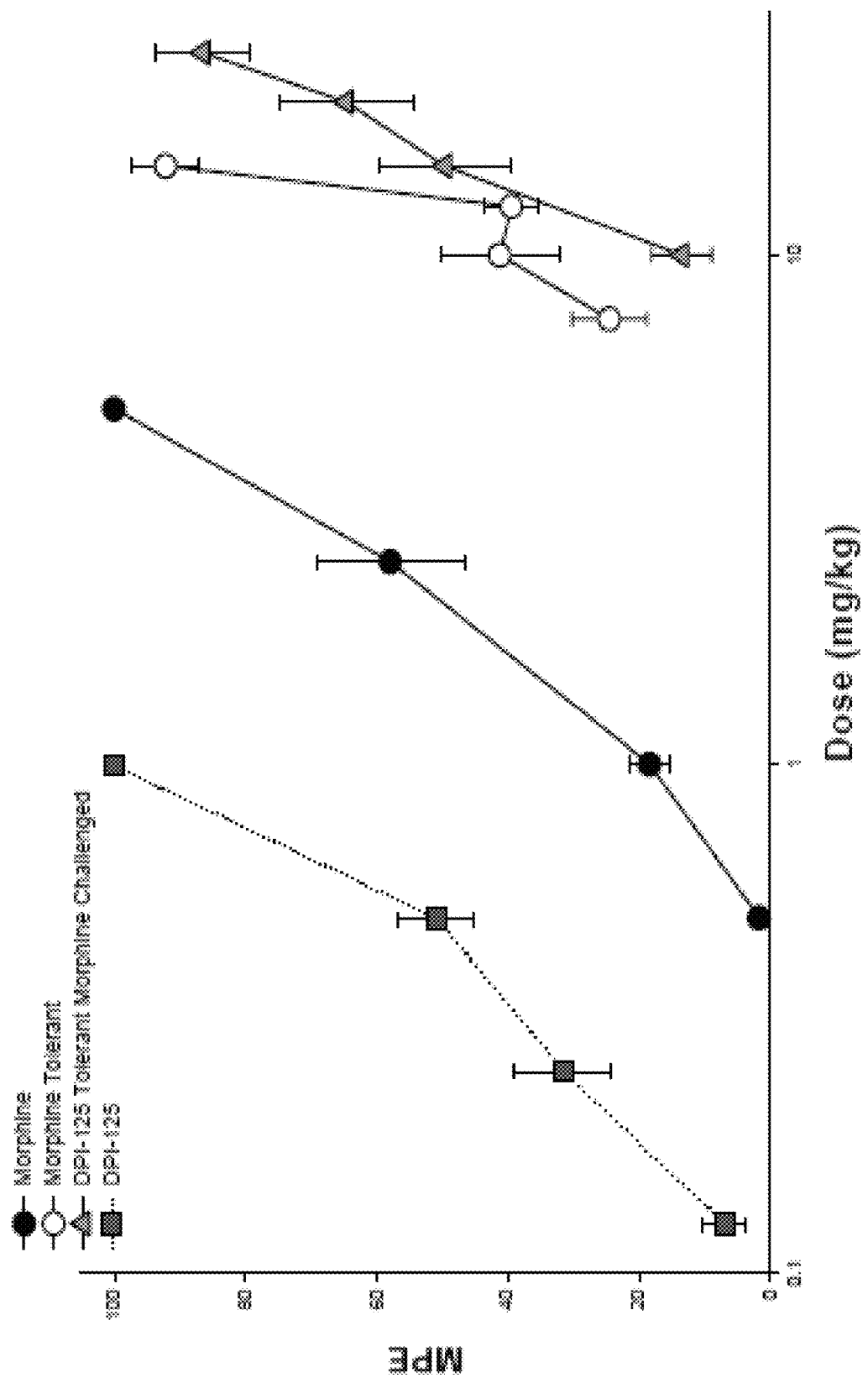
FIG. 3 shows Dose response curves to morphine (s.c.) in male rats tolerant to morphine, DPI-125 or analgesic naïve.

Study 2: The effect of tolerance to DPI-125 or morphine sulfate on the antinociceptive potency of morphine sulfate. FIG. 3 and Table 5 show the dose response curve and ED50 values for morphine sulfate administered subcutaneously to rats that were either naïve to morphine sulfate, tolerant to morphine sulfate or tolerant to DPI-125. The data presented shows the effect of morphine sulfate administration, $R^2$ values for the curve fit ranged were all 0.83 or higher. When administered to naïve animals, morphine sulfate produced antinociception with a mean ED50 value of $2.04^{(1.5-2.84)}$ mg/kg. The potency of morphine sulfate was greatly reduced (by 5.5 fold) when administered to animals tolerant to morphine sulfate. In this case the ED50 value was $11.26^{(8.1-15.6)}$ mg/kg. The administration of morphine sulfate to animals tolerant to DPI-125 showed an even greater reduction in antinociceptive potency of morphine sulfate (7.8 fold) with an ED50 value of $15.82^{(13.25-18.9)}$ mg/kg.

Figure 4:
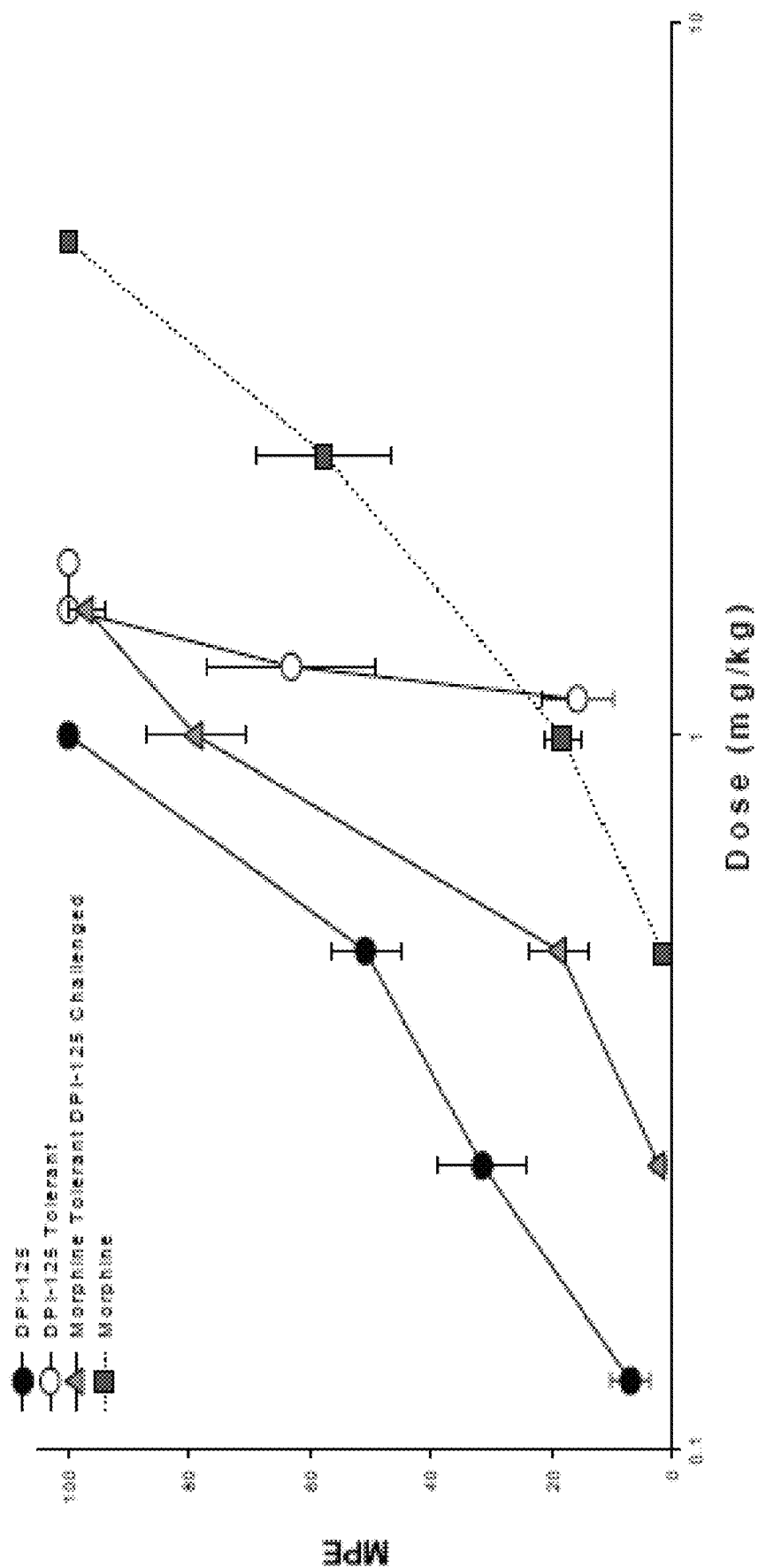
FIG. 4 shows Dose response curves of DPI-125 in male rats tolerant to DPI-125, morphine sulfate or naïve to analgesic.

Study 3: The effect of tolerance to DPI-125 or morphine sulfate on the antinociceptive potency of DPI-125. FIG. 4 and Table 5 show the dose response curve and ED50 values for DPI-125 administered subcutaneously to rats that were either naïve to DPI-125, tolerant to DPI-125 or tolerant to morphine sulfate. The data presented shows the effect of DPI125 administration, R2 values for the curve fit were 0.95 and higher. When administered to naïve animals, DPI-125 produced antinociception with an ED50 value of $0.41^{(0.27-0.63)}$ mg/kg. Following the development of tolerance to DPI-125, however, there was a 2.99 fold decrease in antinociceptive potency with an ED50 value of $1.22^{(1.21-1.23)}$ mg/kg. The antinociceptive potency of DPI-125 was also affected by the induction of tolerance to morphine sulfate. In these animals, DPI-125 was 1.7 fold more potent than in those animals tolerant to DPI-125. However, DPI-125 was 1.8 fold more potent in animals naïve to DPI-125 than those tolerant to morphine sulfate. The ED50 value for antinociception in animals that were tolerant to morphine was $0.72^{(0.67-0.77)}$ mg/kg.

The results presented here from Study 1 demonstrate that both morphine sulfate (10.0 mg/kg/day) and DPI-125 (2.0 mg/kg/day) produce tolerance to their antinociceptive effects. However, DPI-125 tolerance was slower in onset and rate than morphine sulfate such that maximal loss of antinociception occurred with morphine sulfate after approximately half as many doses as with DPI-125. Further to this, morphine sulfate had no antinociceptive effects in animals tolerant to either morphine sulfate or DPI-125. Likewise, DPI-125 had no antinociceptive effects in animals tolerant to DPI-125, but there were significant antinociceptive effects of DPI-125 in animals tolerant to morphine sulfate. Studies 2 and 3 indicate that DPI-125 shows a smaller loss in antinociceptive potency in animals tolerant to morphine sulfate (1.7 fold) or DPI-125 (2.99 fold) than was seen with morphine in animals tolerant to morphine (5.5 fold) or DPI-125 (7.8 fold).

In conclusion: Morphine sulfate and DPI-125 produce antinociceptive tolerance following twice daily subcutaneous doses of 5.0 mg/kg and 1.0 mg/kg respectively. The rate of tolerance development also differed. Maximal tolerance was reached at 5 and 8 days respectively. There was appreciable cross tolerance between morphine sulfate and DPI-125 at these doses, although DPI-125 remained active in animals completely tolerant to morphine sulfate. DPI-125 tolerance produced a 2.99 fold shift in the antinociceptive ED50 of DPI-125. Morphine sulfate tolerance produced a 5.5 fold shift in the antinociceptive ED50 of DPI-125.

REFERENCES

The contents of all references cited herein are incorporated by reference herein for all purposes.

1. Sellers E M, Perrino P J, Colucci S V, Harris S C: Attractiveness of reformulated OxyContin® tablets: assessing comparative preferences and tampering potential. *J Psychopharmacol* 2013, 27:808-816.
2. Kisak E, Buyuktimkin N, Buyuktimkin S, Newsam J, Wen J, Shudo J, Jain A: Compositions and methods for transdermal delivery of hormones and other medicinal agents. U.S. Pat. No. 9,144,553, 2015.
3. Van Buskirk G A, Arsulowicz D, Basu P, Block L, Cai B, Cleary G W, Ghosh T, Gonzalez M A, Kanios D, Marques M, Noonan P K, Ocheltree T, Schwarz P, Shah V, Spencer T S, Tavares L, Ulman K, Uppoor R, Yeoh T: Passive transdermal systems whitepaper incorporating current chemistry, manufacturing and controls (CMC) development principles. *AAPS PharmSciTech* 2012, 13:218-230.
4. Kisak E T, Newsam J M, King-Smith D, Karande P, Mitragotri S: Topical formulation including diclofenac, or a pharmaceutically acceptable salt thereof. U.S. Pat. No. 7,795,309, 2010.
5. Kisak E T, Newsam J M, King-Smith D, Karande P, Mitragotri S: Topical formulation. U.S. Pat. No. 8,343,962, 2013.
6. Hammond F H: In Handbook of Pressure Sensitive Adhesive Technology, 2nd ed. Edited by Satas D: Van Nostrand Reinhold:38-60.
7. Inturrisi C E: Opioid analgesic therapy in cancer pain. In *Advances in Pain Research and Therapy. Vol. 16.* Edited by Foley K M: Raven Press; 1990:133-154.
8. Clotz M A, Nahata M C: Clinical uses of fentanyl, sufentanil, and alfentanil. *Clin Pharm* 1991, 10:581-593.
9. Holder K A, Dougherty T B, Porche V H, Chiang J S: Postoperative pain management. *Int Anesthesiol Clin* 1998, 36:71-86.
10. Gutstein H B, Akil H: Opioid analgesic. In *Goodman and Gilman's The Pharmacological Basis of Therapeutics. 10th Edition.* Edited by Gilman A G, Hardman J G, Limbird L E: McGraw-Hill Companies; 2001:569-619.
11. O'Neill S J, Collins M A, Pettit H O, McNutt R W, Chang K J: Antagonistic modulation between the delta opioid agonist BW373U86 and the mu opioid agonist fentanyl in mice. *J Pharmacol Exp Ther* 1997, 282:271-277.
12. Su Y F, McNutt R W, Chang K J: Delta-opioid ligands reverse alfentanil-induced respiratory depression but not antinociception. *J Pharmacol Exp Ther* 1998, 287:815-823.
13. Funada M, Suzuki T, Narita M, Misawa M, Nagase H (1993). Blockade of morphine reward through the activation of kappa-opioid receptors in mice. *Neuropharmacol* 32: 1315-1323.
14. Xi Z X, Fuller S A, Stein E A (1998). Dopamine release in the nucleus accumbens during heroin self-administration is modulated by kappa opioid receptors: an in vivo fast-cyclic voltammetry study. *J Pharmacol Exp Ther* 284: 151-161.
15. Bowen C A, Negus S S, Zong R, Neumeyer J L, Bidlack J M, Mello N K (2003). Effects of mixed-action kappa/mu opioids on cocaine self-administration and cocaine discrimination by rhesus monkeys. *Neuropsychopharmacol* 28: 1125-1139.
16. Negus S S, Schrode K, Stevenson G W (2008). Mu/kappa opioid interactions in rhesus monkeys: implications for analgesia and abuse liability. *Exp Clin Psychopharmacol* 16: 386-399.
17. Pan Z Z (1998). mu-Opposing actions of the kappa-opioid receptor. *Trends Pharmacol Sci* 19: 94-98.
18. Wang Y H, Sun J F, Tao Y M, Chi Z Q, Liu J G (2010). The role of kappa-opioid receptor activation in mediating antinociception and addiction. *Acta Pharmacol Sin* 31: 1065-1070.
19. Xi Z X, Fuller S A, Stein E A (1998). Dopamine release in the nucleus accumbens during heroin self-administration is modulated by kappa opioid receptors: an in vivo fast-cyclic voltammetry study. *J Pharmacol Exp Ther* 284: 151-161.
20. Gengo P J, Pettit H O, O'Neill S J, Wei K, McNutt R, Bishop M J, Chang K J: DPI-3290 [(+)-3-((alpha-R)-alpha-((2S,5R)-4-allyl-2,5-dimethyl-1-piperazinyl)-3-hydroxybenzyl)-N-(3-fluorophenyl)-N-methylbenzamide]. I. A mixed opioid agonist with potent antinociceptive activity. *J Pharmacol Exp Ther* 2003, 307:1221-1226.
21. Gengo P J, Pettit H O, O'Neill S J, Su Y F, McNutt R, Chang K J: DPI-3290 [(+)-3-((alpha-R)-alpha-((2S,5R)-4-Allyl-2,5-dimethyl-1-piperazinyl)-3-hydroxyb enzyl)-N-(3-fluorophenyl)-N-methylbenzamide]. II. A mixed opioid agonist with potent antinociceptive activity and limited effects on respiratory function. *J Pharmacol Exp Ther* 2003, 307:1227-1233.
22. Gengo P J, Chang K-W: Mixed opioid receptor agonists as a new class of agents for the treatment of moderate to severe pain. I. In The Delta Receptor. Edited by Chang K-J, Porreca F, Woods J H: Marcel Dekker; 2004:231-244.
23. Brito R, Sheth S, Mukherjea D, Rybak L P and Ramkumar V (2014) TRPV1: A Potential Drug Target for Treating Various Diseases. *Cells* 3:517-545.
24. Eisenach J C, Curry R, Tong C, Houle T T and Yaksh T L (2010) Effects of intrathecal ketorolac on human experimental pain. *Anesthesiology* 112:1216-1224.
25. Lazar J, Gharat L, Khairathkar-Joshi N, Blumberg P M and Szallasi A (2009) Screening TRPV1 antagonists for the treatment of pain: lessons learned over a decade. *Expert Opin Drug Discov* 4:159-180.
26. Ding H, Czoty P W, Kiguchi N, Cami-Kobeci G, Sukhtankar D D, Nader M A, Husbands S M and Ko M C (2016) A novel orvinol analog, BU08028, as a safe opioid analgesic without abuse liability in primates. *Proc Natl Acad Sci USA* 113:E5511-5518.
27. Hu E, Calo G, Guerrini R and Ko M C (2010) Long-lasting antinociceptive spinal effects in primates of the novel nociceptin/orphanin FQ receptor agonist UFP-112. *Pain* 148:107-113.
28. Ko M C, Terner J, Hursh S, Woods J H and Winger G (2002) Relative reinforcing effects of three opioids with different durations of action. *J Pharmacol Exp Ther* 301:698-704.
29. Ding H, Hayashida K, Suto T, Sukhtankar D D, Kimura M, Mendenhall V and Ko M C (2015) Supraspinal actions of nociceptin/orphanin FQ, morphine and substance P in regulating pain and itch in non-human primates. *Br J Pharmacol* 172:3302-3312.
30. Ko M C and Naughton N N (2009) Antinociceptive effects of nociceptin/orphanin FQ administered intrathecally in monkeys. *J Pain* 10:509-516.
31. Lee H and Ko M C (2015)Distinct functions of opioid-related peptides and gastrin-releasing peptide in regulating itch and pain in the spinal cord of primates. *Sci Rep* 5:11676.
32. Richardson N R and Roberts D C (1996) Progressive ratio schedules in drug self-administration studies in rats: a method to evaluate reinforcing efficacy. *Journal of neuroscience methods* 66:1-11.

33. Rowlett J K (2000) A labor-supply analysis of cocaine self-administration under progressive-ratio schedules: antecedents, methodologies, and perspectives. *Psychopharmacology* (*Berl*) 153:1-16.
34. Lavonas E J, Severtson S G, Martinez E M, Bucher-Bartelson B, Le Lait M C, Green J L, Murrelle L E, Cicero T J, Kurtz S P, Rosenblum A, Surratt H L and Dart R C (2014) Abuse and diversion of buprenorphine sublingual tablets and film. *Journal of substance abuse treatment* 47:27-34.
35. Cheng Y and Prusoff W H (1973) Relationship between the inhibition constant (K1) and the concentration of inhibitor which causes 50 percent inhibition (I50) of an enzymatic reaction. *Biochem Pharm* 22:3099-3108.

TABLE 1

The Dosing Groups for Study 2

| Group No. | No. of 1.1.1.1.1. | Test Article | Total Daily Dose (mg/kg/day) | Dose (mg/kg BID) | Volume (ml/kg) | Concentration (mg/ml) |
|---|---|---|---|---|---|---|
| 1 | 6 | Control | Days 1 to 6 - 0 | 0.0 | 1.0 | 0.0 |
|   |   | Morphine Sulfate | Day 7 - 1.0 | 0.5 | 1.0 | 0.5 |
| 2 | 6 | Control | Days 1 to 6 - 0 | 0.0 | 1.0 | 0.0 |
|   |   | Morphine Sulfate | Day 7 - 2.0 | 1.0 | 1.0 | 1.0 |
| 3 | 6 | Control | Days 1 to 6 - 0 | 0.0 | 1.0 | 0.0 |
|   |   | Morphine Sulfate | Day 7 -5.0 | 2.5 | 1.0 | 2.5 |
| 4 | 6 | Morphine Sulfate | Days 1 to 6 - 10.0 | 5.0 | 1.0 | 5.0 |
|   |   | Morphine Sulfate | Day 7 - 15.0 | 7.5 | 1.0 | 7.5 |
| 5 | 6 | Morphine Sulfate | Days 1 to 6 - 10.0 | 5.0 | 1.0 | 5.0 |
|   |   | Morphine Sulfate | Day 7 - 20.0 | 10.0 | 1.0 | 10.0 |
| 6 | 6 | Morphine Sulfate | Days 1 to 6 - 10.0 | 5.0 | 1.0 | 5.0 |
|   |   | Morphine Sulfate | Day 7 - 25.0 | 12.5 | 1.0 | 12.5 |
| 7 | 6 | Morphine Sulfate | Days 1 to 6 - 10.0 | 5.0 | 1.0 | 5.0 |
|   |   | Morphine Sulfate | Day 7 - 30.0 | 15.0 | 1.0 | 15.0 |
| 8 | 6 | Morphine Sulfate | Days 1 to 6 - 10.0 | 5.0 | 1.0 | 5.0 |
|   |   | DPI-125 | Day 7 - 0.5 | 0.25 | 1.0 | 0.25 |
| 9 | 6 | Morphine Sulfate | Davs 1 to 6 - 10.0 | 5.0 | 1.0 | 5.0 |
|   |   | DPI-125 | Day 6 - 1.0 | 0.5 | 1.0 | 0.5 |
| 10 | 6 | Morphine Sulfate | Days 1 to 5 - 10.0 | 5.0 | 1.0 | 5.0 |
|   |   | DPI-125 | Day 7 - 2.0 | 1.0 | 1.0 | 1.0 |
| 11 | 6 | Morphine Sulfate | Davs 1 to 6 - 10.0 | 5.0 | 1.0 | 5.0 |
|   |   | DPI-125 | Day 7 - 3.0 | 1.5 | 1.0 | 1.5 |

TABLE 2

Dosing Groups for Study 3

| Group No. | No. of Rats | Test Article | Total Daily Dose | Dose (mg/kg BID) | Volume (ml/kg) | Concentration (mg/ml) |
|---|---|---|---|---|---|---|
| 12 | 6 | Control | Days 1 to 6 - 0 | 0.0 | 1.0 | 0.0 |
|   |   | DPI-125 (D) | Day 7 - 0.25 | 0.125 | 1.0 | 0.125 |
| 13 | 6 | Control | Days 1 to 6 - 0 | 0.0 | 1.0 | 0.0 |
|   |   | DPI-125 (D) | Day 7 - 0.50 | 0.25 | 1.0 | 0.25 |
| 14 | 6 | Control | Days 1 to 6 - 0 | 0.0 | 1.0 | 0.0 |
|   |   | DPI-125 (D) | Day 7 - 1.0 | 0.5 | 1.0 | 0.5 |
| 15 | 6 | DPI-125 (D) | Days 1 to 6 - 2.0 | 1.0 | 1.0 | 1.0 |
|   |   | DPI-125 (D) | Day 7 - 2.25 | 1.125 | 1.0 | 1.125 |
| 16 | 6 | DPI-125 (D) | Days 1 to 6 - 2.0 | 1.0 | 1.0 | 1.0 |
|   |   | DPI-125 (D) | Day 7 - 2.5 | 1.25 | 1.0 | 1.25 |
| 17 | 6 | DPI-125 (D) | Days 1 to 6 - 2.0 | 1.0 | 1.0 | 1.0 |
|   |   | DPI-125 (D) | Day 7 - 3.0 | 1.5 | 1.0 | 1.5 |
| 18 | 6 | DPI-125 (D) | Davs 1 to 6 - 2.0 | 1.0 | 1.0 | 1.0 |
|   |   | DPI-125 (D) | Day 7 - 3/5 | 1.75 | 1.0 | 1.75 |
| 19 | 6 | DPI-125 (D) | Days 1 to 6 - 2.0 | 1.0 | 1.0 | 1.0 |
|   |   | Morphine | Day 7 - 20.0 | 10.0 | 1.0 | 10.0 |

TABLE 2-continued

Dosing Groups for Study 3

| Group No. | No. of Rats | Test Article | Total Daily Dose | Dose (mg/kg BID) | Volume (ml/kg) | Concentration (mg/ml) |
|---|---|---|---|---|---|---|
| 20 | 6 | DPI-125 (D) Sulfate | Days 1 to 6 - 2.0 | 1.0 | 1.0 | 1.0 |
|   |   | Morphine Sulfate | Day 7 - 30.0 | 15.0 | 1.0 | 15.0 |
| 21 | 6 | DPI-125 (D) Sulfate | Days 1 to 6 - 2.0 | 1.0 | 1.0 | 1.0 |
|   |   | Morphine Sulfate | Day 7 - 40.0 | 20.0 | 1.0 | 20.0 |
| 22 | 6 | DPI-125 (D) Sulfate | Days 1 to 6 - 2.0 | 1.0 | 1.0 | 1.0 |
|   |   | Morphine Sulfate | Day 7 - 50.0 | 25.0 | 1.0 | 25.0 |

TABLE 3

The Antinociceptive Effects of Repeated Morphine Doses

Development of Morphine Tolerance

| Day | 1 | 1.25 | 2 | 2.25 | 3 | 3.25 | 4 | 4.25 | 5 | 5.25 |
|---|---|---|---|---|---|---|---|---|---|---|
| Dose | 1 | 2 | 3 | 4 | 5 | 6 | 7 | 8 | 9 | 10 |

20 minutes Post-drug

| | | | | | | | | | | |
|---|---|---|---|---|---|---|---|---|---|---|
| Mean MPE | 100.0 | 100.0 | 78.9 | 56.6 | 33.8 | 32.9 | 23.7 | 7.0 | 3.1 | 5.3 |
| s.e.m. | 0.0 | 0.0 | 8.2 | 10.8 | 8.9 | 8.9 | 7.3 | 2.9 | 1.3 | 1.5 |

30 minutes Post Drug

| | | | | | | | | | | |
|---|---|---|---|---|---|---|---|---|---|---|
| Mean MPE | 100.0 | 100.0 | 75.9 | 57.9 | 46.5 | 24.1 | 20.6 | 5.7 | 2.2 | 3.9 |
| s.e.m. | 0.0 | 0.0 | 9.0 | 7.8 | 9.4 | 7.5 | 8.5 | 1.8 | 1.1 | 1.0 |

Challenge Doses to Morphine Tolerant

| Day | 6 | 6.25 | 7 | 7.25 | | 6 | 6.25 | 7 | 7.25 |
|---|---|---|---|---|---|---|---|---|---|
| Challenge Dose | 1 | 2 | 3 | 4 | | 1 | 2 | 3 | 4 |
| | Morphine Challenge (20 min) | | | | | DPI-125 Challenge (20 min) | | | |
| Mean MPE | 4.4 | 0.9 | 0.0 | 2.6 | Mean MPE | 64.9 | 81.6 | 50.9 | 30.7 |
| s.e.m. | 1.8 | 1.0 | 0.0 | 1.3 | s.e.m. | 13.9 | 13.8 | 13.3 | 16.7 |
| | Morphine Challenge (30 min) | | | | | DPI-125 Challenge (30 min) | | | |
| Mean MPE | 4.4 | 2.6 | 0.9 | 1.8 | Mean MPE | 80.7 | 42.1 | 57.0 | 26.3 |
| s.e.m. | 1.8 | 1.3 | 1.0 | 1.2 | s.e.m. | 16.7 | 20.4 | 19.9 | 17.6 |

TABLE 4

The Antinociceptive Effects of Repeated DPI-125 Doses

Development of DPI-125 Tolerance

| Day | 1 | 1.25 | 2 | 2.25 | 3 | 3.25 | 4 | 4.25 | 5 | 5.25 | 6 | 6.25 |
|---|---|---|---|---|---|---|---|---|---|---|---|---|
| Dose | 1 | 2 | 3 | 4 | 5 | 6 | 7 | 8 | 9 | 10 | 11 | 12 |

20 minutes Post-drug

| | | | | | | | | | | | | |
|---|---|---|---|---|---|---|---|---|---|---|---|---|
| Mean MPE | 100.0 | 100.0 | 99.1 | 79.8 | 84.7 | 81.1 | 70.6 | 75.0 | 75.9 | 47.4 | 34.2 | 37.7 |
| s.e.m. | 0.0 | 0.0 | 0.9 | 7.9 | 10.4 | 9.2 | 12.9 | 10.6 | 9.9 | 12.4 | 13.0 | 13.3 |

30 minutes Post Drug

| | | | | | | | | | | | | |
|---|---|---|---|---|---|---|---|---|---|---|---|---|
| Mean MPE | 100.0 | 100.0 | 100.0 | 88.2 | 66.7 | 69.7 | 72.8 | 51.3 | 40.8 | 28.5 | 21.1 | 11.8 |
| s.e.m. | 0.0 | 0.0 | 0.0 | 5.1 | 11.4 | 11.8 | 11.1 | 9.3 | 11.7 | 9.7 | 8.0 | 8.3 |

TABLE 4-continued

The Antinociceptive Effects of Repeated DPI-125 Doses

| | Challenge Doses to DPI-125 Tolerant | | | | | | | | |
|---|---|---|---|---|---|---|---|---|---|
| Day | 7 | 7.25 | 8 | 8.25 | | 7 | 7.23 | 8 | 8.25 |
| Challenge Dose | 1 | 2 | 3 | 4 | | 1 | 2 | 3 | 4 |
| | Morphine Challenge (20 min) | | | | | DPI-125 Challenge (20 min) | | | |
| Mean MPE | 1.76 | 0.00 | 3.51 | 0.88 | Mean MPE | 8.77 | 22.82 | 9.65 | 1.76 |
| s.e.m. | 1.92 | 0.00 | 1.21 | 0.96 | s.e.m. | 3.22 | 6.78 | 3.13 | 1.92 |
| | Morphine Challenge (30 min) | | | | | DPI-125 Challenge (30 min) | | | |
| MeanMPE | 2.63 | 1.75 | 0.00 | 0.00 | Mean MPE | 3.51 | 7.90 | 2.63 | 0.88 |
| s.e.m. | 1.29 | 1.21 | 0.00 | 0.00 | s.e.m. | 1.92 | 2.88 | 2.88 | 0.96 |

TABLE 5

Antinociceptive Effects of Repeated Morphine and DPI-125 dosing (Studies 2 & 3)

| Drug Treatment | $ED_{50}$ | Confidence Interval | $R^2$ | Fold Change |
|---|---|---|---|---|
| Morphine to naive animals | 2.037 | 1.509-2.750 | 0.98 | |
| Morphine to morphine tolerant animals | 11.26 | 8.115-15.64 | 0.83 | 5.5 |
| Morphine to DPI-125 tolerant animals | 15.82 | 13.25-18.90 | 0.98 | 7.8 |
| DPI-125 to naïve animals | 0.407 | 0.265-0.625 | 0.95 | |
| DPI-125 to DPI-125 tolerant animals | 1.218 | 1.211-1.226 | 0.99 | 3.0 |
| DPI-125 to morphine tolerant animals | 0.717 | 0.671-0.766 | 0.99 | 1.8 |

That which is claimed is:

1. A method to overcome tolerance of an opioid or an opioid like compound, the method comprising administering a compound having the structure of formula (I):

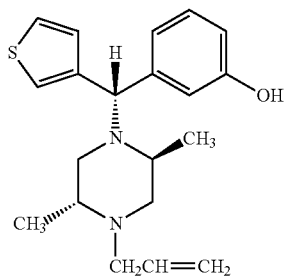

(I)

having the IUPAC name of (−)3-((S)-((2S,5R)-4-allyl-2,5-dimethyl-1-piperazinyl)(3-thienyl)methyl)phenol, or pharmaceutically acceptable esters or salts thereof.

2. The method according to claim 1, wherein the opioid or opioid like compound is selected from the group of morphine, fentanyl, cocaine, heroin, opium, amphetamine, and methamphetamine.

3. The method according to claim 1, wherein the opioid or opioid like compound is selected from the group of codeine, thebaine, dihydrocodeine, hydrocodone, hydromorphone, nicomorphine, oxycodone, oxymorphone, alphamethylfentanyl, alfentanil, sufentanil, remifentanil, carfentanyl, ohmefentanyl, nocaine, pethidine (meperidine), ketobemidone, MPPP, allylprodine, prodine, PEPAP, propoxyphene, dextropropoxyphene, dextromoramide, bezitramide, piritramide, methadone, dipipanone, levo-alphacetylmethadol (LAAM), loperamide, diphenoxylate, pentazocine, phenazocine, buprenorphine, etorphine, butorphanol, nalbuphine, levorphanol, levomethorphan, dezocine, lefetamine, tilidine, tramadol, propoxyphene, or oxycodone.

4. The method according to claim 1, wherein the compound having the structure of formula (I) is administered in a dose of from 0.01 microgram (μg) to 50 milligrams (mg) per kilogram body weight of the recipient.

5. A method to reduce or attenuate negative withdrawal symptoms caused by withdrawal from an opioid or an opioid like compound, the method comprising administering a compound having the structure of formula (I):

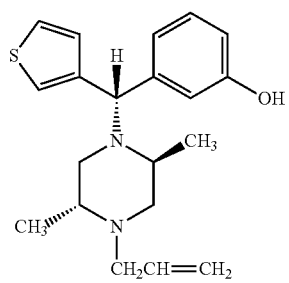

(I)

having the IUPAC name of (−)3-((S)-((2S,5R)-4-allyl-2,5-dimethyl-1-piperazinyl)(3-thienyl)methyl)phenol, or pharmaceutically acceptable esters or salts thereof.

6. The method according to claim 5, wherein the negative withdrawal symptoms comprise sweating, racing heart, palpitations, muscle tension, tightness in the chest, difficulty breathing, tremor, nausea, vomiting, diarrhea, grand mal seizures, heart attacks, strokes, hallucinations and/or delirium tremens (DTs).

7. The method according to claim 5, wherein the opioid or opioid like compound is selected from the group of morphine, fentanyl, cocaine, heroin, opium, amphetamine, and methamphetamine.

8. The method according to claim 5, wherein the opioid or opioid like compound is selected from the group of codeine, thebaine, dihydrocodeine, hydrocodone, hydromorphone, nicomorphine, oxycodone, oxymorphone, alphamethylfentanyl, alfentanil, sufentanil, remifentanil, carfentanyl, ohmefentanyl, nocaine, pethidine (meperidine), ketobemidone, MPPP, allylprodine, prodine, PEPAP, propoxyphene, dextropropoxyphene, dextromoramide, bezitramide, piritramide, methadone, dipipanone, levo-alphacetylmethadol (LAAM), loperamide, diphenoxylate, pentazocine, phenazocine, buprenorphine, etorphine, butorphanol, nalbuphine, levorphanol, levomethorphan, dezocine, lefetamine, tilidine, tramadol, propoxyphene, or oxycodone.

9. The method according to claim 5, wherein the compound having the structure of formula (I) is administered in a dose of from 0.01 microgram (µg) to 50 milligrams (mg) per kilogram body weight of the recipient.

\* \* \* \* \*